United States Patent
Woerz et al.

(10) Patent No.: US 11,180,467 B2
(45) Date of Patent: Nov. 23, 2021

(54) PROPENE RECOVERY BY SCRUBBING WITH A SOLVENT/WATER MIXTURE

(71) Applicant: BASF SE, Ludwigshafen am Rhein (DE)

(72) Inventors: Nicolai Tonio Woerz, Ludwigshafen (DE); Ulrich Mueller, Ludwigshafen (DE); Andrei-Nicolae Parvulescu, Ludwigshafen (DE); Dominic Riedel, Ludwigshafen (DE); Marvin Kramp, Ludwigshafen (DE); Daniel Urbanczyk, Ludwigshafen (DE); Ulrike Wegerle, Worms (DE); Christian Mueller, Ludwigshafen (DE); Bernd Metzen, Ludwigshafen (DE); Markus Weber, Ludwigshafen (DE); Joaquim Henrique Teles, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 62 days.

(21) Appl. No.: 16/500,313

(22) PCT Filed: Apr. 13, 2018

(86) PCT No.: PCT/EP2018/059516
§ 371 (c)(1),
(2) Date: Oct. 2, 2019

(87) PCT Pub. No.: WO2018/197234
PCT Pub. Date: Nov. 1, 2018

(65) Prior Publication Data
US 2021/0002241 A1 Jan. 7, 2021

(30) Foreign Application Priority Data
Apr. 24, 2017 (EP) ..................... 17167780

(51) Int. Cl.
*C07D 301/32* (2006.01)
*C07D 301/19* (2006.01)
*C07D 301/12* (2006.01)

(52) U.S. Cl.
CPC ......... *C07D 301/32* (2013.01); *C07D 301/19* (2013.01)

(58) Field of Classification Search
CPC ... C07D 301/32; C07D 301/19; C07D 301/12
See application file for complete search history.

(56) References Cited

U.S. PATENT DOCUMENTS

| | | |
|---|---|---|
| 2003/0109725 A1 | 6/2003 | Hofen et al. |
| 2004/0192946 A1 | 9/2004 | Teles et al. |
| 2005/0245751 A1 | 11/2005 | Bender et al. |
| 2006/0167287 A1 | 7/2006 | Bassler et al. |

FOREIGN PATENT DOCUMENTS

| | | |
|---|---|---|
| CA | 2256395 A1 | 12/1997 |
| CN | 103724299 A | 4/2014 |
| CN | 103172486 B | 7/2015 |
| EP | 1 122 246 A1 | 8/2001 |
| EP | 1 122 249 A1 | 8/2001 |
| EP | 1 485 366 B1 | 6/2006 |
| EP | 1417192 B1 | 2/2008 |
| RU | 2324689 C2 | 5/2008 |
| RU | 2332409 C2 | 8/2008 |
| RU | 2016105802 A | 8/2017 |
| RU | 2016105805 A | 8/2017 |
| WO | WO 02/102496 A1 | 12/2002 |
| WO | WO 2004/020423 A1 | 3/2004 |
| WO | WO 2004/037390 A1 | 5/2004 |
| WO | WO 2004/037802 A1 | 5/2004 |
| WO | 2004/092150 A1 | 10/2004 |
| WO | 2004/099166 A1 | 11/2004 |
| WO | 2015/010990 A1 | 1/2015 |
| WO | 2015/010991 A1 | 1/2015 |
| WO | WO 2015/049327 A1 | 4/2015 |

OTHER PUBLICATIONS

International Search Report dated Jun. 29, 2018 in PCT/EP2018/059516 filed Apr. 13, 2018, 3 pages.
International Preliminary Report on Patentability and Written Opinion of the International Searching Authority dated Nov. 7, 2019 in PCT/EP2018/059516 filed Apr. 13, 2018, 7 pages.
T. Holderbaum, et al. "PSRK: A Group Contribution Equation of State Based on UNIFAC", Fluid Phase Equilibria, vol. 70, 1991, pp. 251-265.

*Primary Examiner* — Sun Jae Yoo
(74) *Attorney, Agent, or Firm* — Faegre Drinker Biddle & Reath LLP

(57) ABSTRACT

The invention relates to a process for preparing propylene oxide, comprising (i) providing a stream comprising propene, propane, hydrogen peroxide or a source of hydrogen peroxide, water, and an organic solvent; (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and the organic solvent; (iii) removing an effluent stream from the epoxidation zone, the effluent stream comprising propene, propane, propylene oxide, water, and the organic solvent; (iv) separating propene and propane from the effluent stream by distillation, comprising subjecting the effluent stream to distillation conditions in a distillation unit, obtaining a gaseous stream (S1) which is enriched in propene and propane compared to the effluent stream subjected to distillation conditions, and a liquid bottoms stream (S2) which is enriched in propylene oxide, water and organic solvent compared to the effluent stream subjected to distillation conditions; (v) separating propane from the stream (S1) in a separation zone, comprising subjecting the stream (S1) to washing conditions in a scrubber, wherein a solvent mixture comprising organic solvent and water is added as entraining agent, obtaining a bottoms stream (S3), which comprises organic solvent, water and at least 70 weight-% of the propene comprised in (S1); and a gaseous top stream (S4), which comprises at least 5 weight-% of the propane comprised in stream (S1).

15 Claims, 5 Drawing Sheets

PROPENE RECOVERY BY SCRUBBING WITH A SOLVENT/WATER MIXTURE

Figure 1:
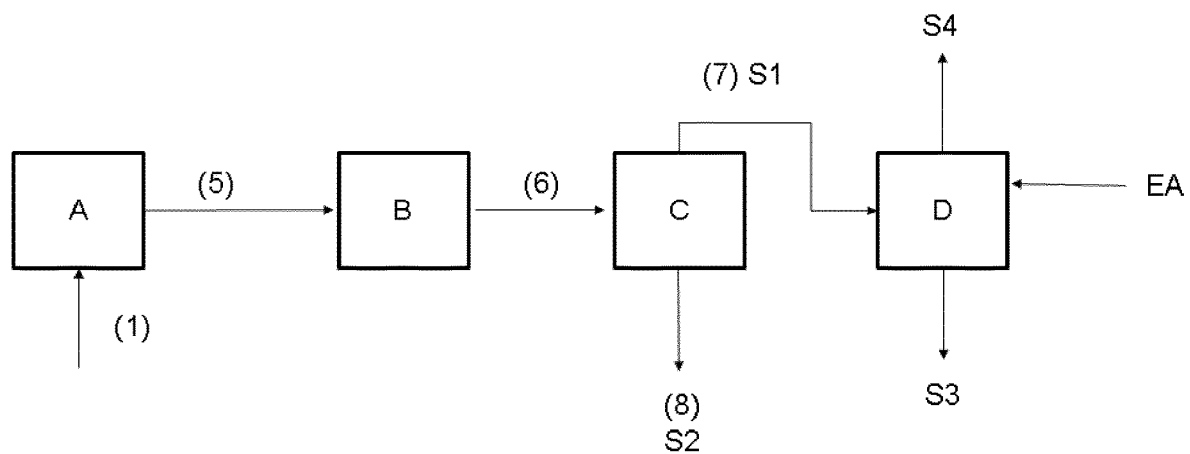

The present invention relates to a process for preparing propylene oxide from a stream comprising propene, propane, hydrogen peroxide or a source of hydrogen peroxide, water and an organic solvent, wherein propene is reacted with the hydrogen peroxide or the source of hydrogen peroxide in an epoxidation zone comprising an epoxidation catalyst comprising a titanium zeolite, wherein propene and propane are separated from the effluent stream removed from the epoxidation zone by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, and the further components water and organic solvent compared to the effluent stream subjected to distillation conditions; and propane is separated from the stream S1 in a separation zone, comprising subjecting the stream S1 to washing conditions in a scrubber, wherein a solvent mixture comprising organic solvent and water is added as entraining agent, obtaining a bottoms stream S3, which comprises organic solvent, water and at least 70 weight-% of the propene comprised in S1; and a gaseous top stream S4, which comprises at least 5 weight-% of the propane comprised in stream S1.

Propylene oxide is an important intermediate in the chemical industry. A suitable process for the preparation of propylene oxide starts from propene and makes use of hydrogen peroxide as oxidizing agent, of a solvent and of an epoxidation catalyst comprising a titanium zeolite. Due to its importance for industrial-scale processes, it is desired to carry out the epoxidation reaction as efficiently as possible. The epoxidation reaction results in a mixture comprising solvent, water and propylene oxide. Since the epoxidation is usually carried out with an excess on propene, the resulting mixture comprises solvent, water and propylene oxide, and also varying amounts of propene. Especially in industrial-scale continuous processes for the epoxidation of propene in a solvent, one feature of the overall process is the recycling of the unconsumed propene. Since propylene oxide is volatile, the separation of non-reacted propene is challenging if the entrainment of propylene oxide is to be avoided. Furthermore, the propene used usually contains measurable quantities of propane. For example, commercially available propene may be either a polymer grade propene or a chemical grade propene. Typically, polymer grade propene has a propane content in the range of from 0.2 to 1 weight-% and chemical grade propene typically has a propane content in the range of from 2 to 8 weight-%. The separation of propene from propane is conventionally done by low temperature and/or high-pressure distillation, which makes this separation of propene and propane very energy-expensive because of the low relative volatility.

WO 2004/037802 A1 relates to a method for continuously returning an olefin which has not been reacted with hydroperoxide in order to form oxiranes during the epoxidation of olefins. Said olefin is contained in the flow of waste gas which is produced during epoxidation. The method comprises a steps of compressing and cooling a flow of waste gas, which is produced during epoxidation, and a step of separating the unreacted olefin from the flow of waste gas by distillation, wherein the distillation step can be combined with a further distillation in order to separate propene from propane, i.e. a separation of propene and propane in a C3 splitter.

WO 02/102496 A1 discloses a process for the epoxidation of propene with hydrogen peroxide in an alcoholic solvent in the presence of a catalyst, wherein a gas stream comprising unreacted propene, propene oxide and oxygen from the decomposition of the hydrogen peroxide is separated from the reaction mixture and the combustible components in said gas stream, i.e. propene and propene oxide, are separated from oxygen and thus recovered by selective absorption of these combustible components in a solvent, whereby during the absorption the gas phase is dispersed in a continuous liquid phase of the solvent.

Oxygen separation is also dealt with in EP 1 122 246 A1 and EP 1 485 366 B1. EP 1 485 366 B1 relates to a process for the catalytic epoxidation of olefins in at least one reaction stage, wherein an exit gas stream containing olefin oxide, unreacted olefin, oxygen and inert gas is removed from the reactor. The exit gas stream is brought into contact in an absorption unit with the same solvent as used in the reaction stage and two streams are removed from the absorption unit: a solvent stream loaded with olefin and olefin oxide and a gas stream containing oxygen and the inert gas. EP 1 122 246 A1 also relates to a process for the catalytic epoxidation of olefins in one reaction stage, wherein an exit gas stream is obtained which contains olefin oxide, unreacted olefin and oxygen. This exit gas stream is brought into contact in an absorption unit with the same solvent as used in the reaction stage and a solvent stream loaded with olefin and olefin oxide is drawn off from the absorption unit and an exit gas stream containing oxygen is discharged. From the liquid exit stream from the epoxidation, which contains propane, propene, propylene oxide, water and solvent, a stream containing propene and propene is separated, which is thereafter worked up in order to separate propane from propane. The unreacted propene is recycled to the epoxidation.

All these documents have in common that either the propane/propene separation is not thematised or the separation requires a, sometimes multiple, distillation approach, which is consumptive with respect to energy and apparatuses.

It was therefore an object of the present invention to provide a process for the recovery of propene and thus also the separation of propane from propene, which is efficient and simple and allows to essentially avoid a multi-distillation approach. The process should be economically advantageous and should especially allow to reduce energy consumption and number of required stages.

Surprisingly, it was found that if in the destillative separation of propene and propane a suitable entraining agent is used, it is possible to separate these two C3 components from each other to a convenient extent, without need for further separation stages.

Therefore, the present invention relates to a process for preparing propylene oxide, comprising
(i) providing a stream comprising propene, propane, hydrogen peroxide or a source of hydrogen peroxide, water, and an organic solvent;
(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and the organic solvent;

(iii) removing an effluent stream from the epoxidation zone, the effluent stream comprising propene, propane, propylene oxide, water, and the organic solvent;

(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and organic solvent compared to the effluent stream subjected to distillation conditions;

(v) separating propane from the stream S1 in a separation zone, comprising subjecting the stream S1 to washing conditions in a scrubber, wherein a solvent mixture comprising organic solvent and water is added as entraining agent, obtaining a bottoms stream S3, which comprises organic solvent, water and at least 70 weight-% of the propene comprised in S1; and a gaseous top stream S4, which comprises at least 5 weight-% of the propane comprised in stream S1.

It was surprisingly found that use of a suitable entraining agent in step (v) enables a separation of propene and propane. Since propene accumulates in the liquid phase of the entraining agent, the use of a scrubber with entraining agent in (v) allows a recovery of propene in the sump, which can then be recycled to the process. Propane on the contrary passes over to the liquid phase to a much smaller extent and can thus be eliminated via the gaseous top stream S4, which leaves the scrubber at the top.

Preferably, the process is a continuous process.

Entraining Agent

Generally, there is no specific restriction with respect to the composition of the entraining agent, provided that it comprises organic solvent and water and is able to separate propene and propane.

In the context of the present invention, the uptake of a given compound in a solvent has been connected to the solvent's activity coefficient. Activity coefficient models can be applied to vapor-liquid equilibria with components at significantly subcritical conditions and at a moderate pressure range. For a specific component i and a specific solvent the ratio of the molar concentration of the component in the vapor phase of the solvent ($y_i$) and in the liquid phase of the solvent ($x_i$) is resulting from the ideal ratio of the pure component's vapor pressure ($P_i^0$) to the total pressure (P) and the activity coefficient ($g_i$):

$$(y_i/x_i) = g_i \cdot (P_i^0/P)$$

For a component i a low vapor-liquid ratio corresponding to a high solubility will result if it shows a low activity coefficient in the specific solvent. Therefore for two components i and j, a selectivity $S_{ij}=(g_j/g_i)$ can be defined by the invers ratio of the related activity coefficients parting from the constant ratio of the pure components vapor pressures ($P_j^0$, $P_i^0$) at isothermal conditions.

$$(y_j/x_j)/(y_i/x_i) = (g_j/g_i) \cdot (P_j^0/P_i^0) = S_{ij} \cdot (P_j^0/P_i^0)$$

For screening purposes and in the case of small concentrations in the solvent the selectivity of two components i, j can be approximated by the ratio of the limiting activity coefficients at infinite dilution ($g_i^\infty$, $g_j^\infty$).

$$S_{ij} = (g_j^\infty/g_i^\infty)$$

The thermal separation effect by a specific solvent regarding two components i, j can be limited by a liquid-liquid miscibility gap. The thermodynamic condition regarding a miscibility gap requires the equality of the products of mole fraction ($x_i$) and activity coefficient ($g_i$) for all components in the two liquid phases 1, 2:

$$(x_i \cdot g_i)^{liquid\ phase\ 1} = (x_i \cdot g_i)^{liquid\ phase\ 2}$$

For screening purposes and in the case of a wide miscibility gap and a nearly pure solute (dissolved component) phase (product of solute mole fraction and solute activity coefficient reaches the value of one) the capacity (KAP) of the solvent corresponding to the solubility of the solute in the solvent phase can approximately be estimated by the invers value of the limiting activity coefficient of the solute in the solvent phase. Dividing by the molar weight of the solvent (MW) (in case of a solvent mixture the mole fraction weighted averages) enables an approximative mass based comparison of different solvents regarding a solute component:

$$KAP = x_{solute}^{solvent\ phase} = 1/g_{solute}^{solvent\ phase}$$

$$KAPm = KAP/MW^{solvent}$$

Regarding the separation of propane from the stream S1 in the separation zone according to (v) from the stream S1, the relative capacity for the propene absorption and the relative selectivity against propane and also against $CO_2$, which is also contained in S1, was elaborated on the basis of limiting activity coefficients at 298K, calculated by Cosmo-RS (COSMOthermX, Version C30_1601, developed and copyright by COSMOlogic GmbH&Co.KG, Imbacher Weg 46, 51379 Leverkusen, GERMANY). The parametrization BP_TZVPD_FINE_C30_1601 was applied. The Cosmo-RS calculation is based on an activity coefficient model with ideal gas phase.

Therefore the fugacity and the pressure effect on the gas phase is not considered, the activity coefficient is not depending on the pressure.

Parting from the limiting activity coefficients at infinite dilution ($g^\infty(CO_2)$, $g^\infty(Propane)$ and $g^\infty(Propene)$) at 25° C. selectivity (S) and capacity (KAP, KAPm mass based, considering the molar weight MW in [g/mol] of the solvent mixture, i.e. the mole fraction weighted averages, and criteria were calculated taking into account different amounts of water in the solvents, preferably acetonitrile or methanol. The following criteria were calculated:

$$S_1 = g^\infty(Propane)/g^\infty(Propene)$$

$$S_2 = g^\infty(CO_2)/g^\infty(Propene)$$

$$KAP = 1/g^\infty(Propene)$$

$$KAPm = 1/g^\infty(Propene)/MW(solvent\ mixture) \cdot 1000$$

Tables 3 and 4 shown in the Example section compile the limiting activity coefficients and the selectivity and capacity criteria (mass related capacity multiplied by 1000 for readability) with increasing water concentration (w(g/g) $H_2O$ weight fraction of water) parting from the pure preferred solvents acetonitrile or methanol. It was surprisingly found that with increasing water concentration in suitable solvents, preferably acetonitrile and methanol, the capacity for the propene absorption is diminished and the selectivity against propane is enhanced.

Preferably, the solvent mixture comprising organic solvent and water added as entraining agent in (v) has a capacity KAP with regard to propene at 25° C. in the range from 0.01 to 0.2, preferably in the range from 0.02 to 0.19. Furthermore, the solvent mixture comprising organic solvent and water added as entraining agent in (v) has preferably a mass based capacity KAP$_m$ with regard to propene at 25° C. in the range from 4.4 to 10, preferably in the range from 4.5 to 9, more preferably in the range from 4.6 to 8, more preferably in the range from 4.7 to 7.

Preferably, the solvent mixture comprising organic solvent and water added as entraining agent in (v) has a selectivity S with regard to propene at 25° C. in the range from 1.3 to 3.5, preferably in the range from 1.4 to 3.4, more preferably in the range from 1.5 to 3.3.

Generally, there is no specific restriction with respect to the organic solvent used, provided that it fulfills at least one of the above mentioned criteria, i.e. that at least its capacity KAP, mass based capacity KAP$_m$ or selectivity S lies within the range(s) mentioned above, preferably at least two of these criteria, more preferably it fulfills all three criteria. According to a preferred embodiment, the organic solvent comprised in the solvent mixture used as entraining agent in (v) is selected from the group consisting of acetonitrile, butanone, propanone, cyclopentanone, methylacetate, 1,3-dioxoloane, ethylformate, 1,4-dioxane, 1,3-dioxane, valeronitrile, butyronitrite, methylformate, propionitrile, dimethylcarbonate, dimethylformamide, acetophenone, 1-methoxy-2-propanone, 1-phenyl-2-propanone, 1,1,1,-trifluoro-2-propanone, benzonitrile, 2-(2-methoxyethoxy)ethanol, methanol and mixtures of two or more thereof, preferably from acetonitrile, methanol and mixtures of acetonitrile and methanol, more preferably acetonitrile or methanol.

Generally, no dependency exists regarding the organic solvent used in (v) to the organic solvent present in (i) to (iii). Preferably, the organic solvent comprised in the solvent mixture in (v) is the same organic solvent as comprised in the stream provided in (i).

Generally, there is no specific restriction with respect to the composition of the entraining agent as long as it is able to separate propene and propane. Preferably, the solvent mixture used as entraining agent in (v) comprises at least 0.1 weight-%, preferably at least 1 weight-%, more preferably at least 5 weight-%, more preferably at least 10 weight-%, more preferably at least 15 weight-%, of water based on the total weight of the solvent mixture.

Surprisingly, it was found that increased water content in the entraining agent enables an improved separation of propene and propane, even at a low water content of 1 wt.-%. A further increase of the water content in the entraining agent results in an increase in the weight ratio propene to propane in the bottoms stream S3 since, even if the capacity for the propene absorption diminishes, the selectivity against propene enhances to a larger extent when the water content increases. Thus, the use of a scrubber with entraining agent organic solvent/water allows a recovery of propene in the sump, which can then be recycled to the process.

According to a first preferred embodiment, the present invention relates to a process comprising
  (i) providing a stream comprising propene, propane, hydrogen peroxide or a source of hydrogen peroxide, water, and acetonitrile;
  (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and acetonitrile;
  (iii) removing an effluent stream from the epoxidation zone, the effluent stream comprising propene, propane, propylene oxide, water, and acetonitrile;
  (iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;
  (v) separating propane from the stream S1 in a separation zone, comprising subjecting the stream S1 to washing conditions in a scrubber, wherein a solvent mixture comprising acetonitrile and water is added as entraining agent, obtaining a bottoms stream S3, which comprises acetonitrile, water and at least 70 weight-% of the propene comprised in S1; and a gaseous top stream S4, which comprises at least 5 weight-% of the propane comprised in stream S1.

According to a second preferred embodiment, the present invention relates to a process comprising
  (i) providing a stream comprising propene, propane, hydrogen peroxide or a source of hydrogen peroxide, water, and methanol;
  (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and methanol;
  (iii) removing an effluent stream from the epoxidation zone, the effluent stream comprising propene, propane, propylene oxide, water, and methanol;
  (iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and methanol compared to the effluent stream subjected to distillation conditions;
  (v) separating propane from the stream S1 in a separation zone, comprising subjecting the stream S1 to washing conditions in a scrubber, wherein a solvent mixture comprising methanol and water is added as entraining agent, obtaining a bottoms stream S3, which comprises methanol, water and at least 70 weight-% of the propene comprised in S1; and a gaseous top stream S4, which comprises at least 5 weight-% of the propane comprised in stream S1.

Effluent Stream from Epoxidation

According to (iii), an effluent stream is removed from the epoxidation zone. Generally, there is no specific restriction with respect to the composition of the effluent stream, provided that it comprises propene, propane, propylene oxide, water, and organic solvent. Preferably, at least 95 weight-%, more preferably from 95 to 99.6 weight-%, more preferably from 98 to 99.7 weight-%, more preferably from 99 to 99.8 weight-%, of the effluent stream removed in (iii) consist of propylene oxide, the organic solvent, water, propene, oxygen, and propane. Further components that can be comprised in the effluent stream are acetone, acetaldehyde, formaldehyde, hydroxyacetone, propylene glycol, dipropyleneglycol, tripropyleneglycol, CO, $CO_2$ and secondary organic hydroperoxides.

Preferably, the effluent stream removed in (iii) comprises the propylene oxide in an amount of from 5 to 20 weight-%, preferably from 6 to 18 weight-%, more preferably from 7 to 14 weight-%, based on the total weight of the effluent stream; the organic solvent in an amount of from 55 to 75 weight-%, preferably from 6 to 74 weight-%, based on the total weight of the effluent stream; the water in an amount of from 10 to 25 weight-%, preferably from 15 to 20 weight-%, based on the total weight of the effluent stream; the propene in an amount of from 1 to 5 weight-%, preferably from 3 to 4.5 weight-%, based on the total weight of the effluent stream; oxygen in an amount of from 0.05 to 1 weight-%, preferably from 0.1 to 0.5 weight-%, based on the total weight of the effluent stream; and the propane in an amount of from 0.1 to 2 weight-%, preferably from 0.2 to 1 weight-%, based on the total weight of the effluent stream.

Separation in (iv)

According to (iv), propene and propane are separated from the effluent stream by distillation, comprising subjecting the effluent stream to distillation conditions in a distillation unit, preferably a distillation tower. From this distillation tower, S1 is obtained as gaseous top stream. Preferably, this distillation tower has from 3 to 50, more preferably from 4 to 40, more preferably from 5 to 35, theoretical trays. The distillation tower is preferably operated at a top pressure of from 0.5 to 1.5 bar, more preferably of from 0.9 to 1.3 bar. In order to facilitate said separation task, it was found that it is advantageous to add liquid organic solvent, preferably either liquid acetonitrile or a liquid methanol or a mixture of acetonitrile or methanol with water to the top of the column. It is believed that this external reflux serves as entraining agent which, among others, prevents propylene oxide from being separated via the top of the distillation tower. The entraining agent is taken from a separate tank or from a later process stage. Preferably, the weight ratio of the amount of acetonitrile fed as external reflux to the top of the distillation tower relative to the weight of the effluent stream fed into the distillation tower and to be separated in the distillation tower is in the range of from 0.2:1 to 4:1 preferably from 0.3:1 to 2:1. The temperature of the external reflux is generally in the range of from 2 to 20° C., preferably in the range of from 5 to 15° C.

Depressurization Prior to (iv)

Preferably, prior to (iv), the effluent stream removed according to (iii) is depressurized, preferably to a pressure of from 0.5 to 2.8 bar, more preferably of from 0.6 to 2.5 bar, more preferably of from 0.8 to 1.5 bar. Generally, there is no specific restriction how the effluent stream is depressurized. Preferably, the effluent stream is depressurized into a flash drum. Preferably, from depressurizing the effluent stream, a gaseous stream and a liquid stream are obtained, wherein the gaseous and liquid streams are preferably passed separately to the distillation unit employed according to (iv), preferably to the same theoretical tray of the distillation unit employed according to (iv).

Stream S1

According to (iv), propene and propane are separated from the effluent stream by distillation, comprising subjecting the effluent stream to distillation conditions in a distillation unit, obtaining a gaseous stream S1 which is enriched in propene and propane compared to the effluent stream subjected to distillation conditions.

Generally, there is no specific restriction with respect to the composition of the gaseous stream S1, provided that it comprises propene and propane and is enriched in propene and propane compared to the effluent stream subjected to distillation conditions. Preferably, at least 90 weight-%, preferably from 90 to 96 weight-%, more preferably from 92 to 97 weight-%, more preferably from 95 to 98 weight-% of the gaseous stream S1 obtained in (iv) consist of propene and propane, the rest being mainly oxygen, nitrogen, CO and $CO_2$. According to one preferred embodiment, the gaseous stream S1 obtained in (iv) comprises the propene in an amount of from 85 to 95 weight-%, preferably from 87 to 94 weight-%, more preferably from 90 to 93 weight-%, based on the total weight of the stream S1; and the propane in an amount of from 1 to 10 weight-%, preferably from 3 to 7 weight-%, more preferably from 4 to 6 weight-%, based on the total weight of the stream S1. Preferably, the gaseous stream S1 obtained in (iv) comprises the propene in an amount of from 85 to 95 weight-%, preferably from 87 to 94 weight-%, more preferably from 90 to 93 weight-%, based on the total weight of the stream S1; the propane in an amount of from 1 to 10 weight-%, preferably from 3 to 7 weight-%, more preferably from 4 to 6 weight-%, based on the total weight of the stream S1, water in an amount of from 0 to 1 weight-% based on the total weight of the stream S1, and nitrogen in an amount of from 0.1 to 5 weight-% based on the total weight of the stream S1.

According to a preferred embodiment, the weight ratio propene to propane in the gaseous stream S1 obtained in (iv) is in the range of 5:1 to 100:1, preferably in the range of 6:1 to 80:1, more preferably in the range of 7:1 to 50:1.

Stream S2

According to (iv), propene and propane are separated from the effluent stream by distillation, comprising subjecting the effluent stream to distillation conditions in a distillation unit, obtaining a liquid bottoms stream S2 which is enriched in propylene oxide, water and organic solvent compared to the effluent stream subjected to distillation conditions. Generally, no restrictions regarding the composition of S2 exist provided that it comprises propylene oxide, water and organic solvent and is enriched in propylene oxide, water and organic solvent compared to the effluent stream subjected to distillation conditions. Preferably, at least 90 weight-%, more preferably from 90 to 96 weight-%, more preferably from 92 to 97 weight-%, more preferably from 95 to 98 weight-% of the liquid bottoms stream S2 obtained in (iv) consists of propylene oxide, water and organic solvent.

Stream S3

According to (v), propane is separated from the stream S1 in a separation zone, comprising subjecting the stream S1 to washing conditions in a scrubber, wherein a solvent mixture comprising organic solvent and water is added as entraining agent, obtaining a bottoms stream S3, which comprises organic solvent, water and at least 70 weight-% of the propene comprised in S1. Preferably, at least 90 weight-%, preferably from 90 to 98 weight-%, more preferably from 92 to 98.5 weight-%, more preferably from 95 to 99 weight-% of the bottoms stream S3 obtained in (v) consists of organic solvent, water, propene and propane, CO and $CO_2$. Preferably, the bottoms stream S3 obtained in (v) comprises at least 70 weight-%, more preferably at least 80 weight-%, more preferably at least 90 weight-%, more preferably at least 95 weight-%, of the propene comprised in S1.

According to a preferred embodiment, the weight ratio propene to propane in the bottoms stream S3 obtained in (v) is in the range of 1:1 to 100:1, preferably in the range of 5:1 to 50:1, more preferably in the range of 10:1 to 40:1, more preferably in the range of 15:1 to 30:1.

Stream S4

According to (v), propane is separated from the stream S1 in a separation zone, comprising subjecting the stream S1 to washing conditions in a scrubber, wherein a solvent mixture comprising organic solvent and water is added as entraining agent, obtaining a gaseous top stream S4, which comprises at least 5 weight-% of the propane comprised in stream S1. Preferably, at the outmost 50 weight-%, more preferably 40 weight-%, more preferably 30 weight-%, more preferably 25 weight-% of the gaseous top stream S4 consist of propene and propane. Preferably, the gaseous top stream S4 obtained in (v) comprises at the outmost 30 weight-%, more preferably at the outmost 25 weight-%, more preferably at the outmost 20 weight-%, more preferably at the outmost 10 weight-%, more preferably at the outmost 5 weight-%, more preferably at the outmost 3 weight-%, of the propene comprised in S1.

According to a preferred embodiment, the weight ratio propene to propane in the gaseous top stream S4 obtained in (v) is in the range of 1:1 to 15:1, preferably in the range of 2 to 1 to 15:1, more preferably in the range of 3:1 to 12:1.

Scrubber

According to (v) propane is separated from the stream S1 in a separation zone, comprising subjecting the stream S1 to washing conditions in a scrubber. Generally, there is no specific restriction with respect to the design of the scrubber, provided that is suitable for carrying out the separation of propane from the stream S1. Preferably, the scrubber employed in (v) is a column, preferably having from 2 to 20, more preferably from 3 to 18, more preferably from 5 to 15, theoretical trays.

Generally, no restrictions exist where the entraining agent is fed to the scrubber. Preferably, the solvent mixture comprising organic solvent and water added as entraining agent to the scrubber employed in (v) is added at a theoretical tray above the feed tray of the stream S1, more preferably at a tray in the range of tray 1 to 10, more preferably in the range of tray 1 to 5, more preferably in the range of tray 1 to 3, counted from the top, more preferably at the top of the scrubber (tray 1).

Preferably, the weight ratio of solvent mixture comprising organic solvent and water added as entraining agent to the scrubber employed in (v) per hour to the weight ratio of stream S1 feed to the scrubber per hour is in the range of 1:10 to 10:1, preferably in the range of 1:1 to 10:1, more preferably in the range of 2:1 to 5:1.

Preferably, the scrubber employed in (v) is operated at a top temperature in the range of 10 to 30° C., more preferably in the range of 14 to 26° C., more preferably in the range of 15 to 22° C. Preferably, the scrubber employed in (v) is operated at a sump temperature in the range of 20 to 65° C., more preferably in the range of 25 to 60° C., more preferably in the range of 27 to 50° C. Preferably, the scrubber employed in (v) is operated at a sump pressure of in the range of 1 to 35 bar, more preferably in the range of 5 to 32 bar, more preferably in the range of 10 to 30 bar.

It was surprisingly found that a pressure increase, especially a pressure increase in the range of 5 to 30 bar, results in an increase of the uptake capacity of the organic solvent/water mixture for propene and propane, in that the amount of entraining agent needed at a pressure $p_1$ could be lowered compared to the amount needed at a pressure $p_0$ ($p_1 > p_0$). For example, at a pressure of 30 bar, the amount of entraining agent needed can be lowered to less than 10% of the initial amount at 5 bar. For the preferred entraining agent acetonitrile/water, a pressure increase, preferably in the range of 5 to 30 bar, does not negatively influence the purity of propene in the bottoms stream S3. However, when using methanol/water, the purity of propene in S3 slightly decreases with increasing pressure.

According to (v), propane is separated from the stream S1 in a separation zone, comprising subjecting the stream S1 to washing conditions in a scrubber. Generally, there are no specific restrictions regarding the design of the separation zone, provided that it comprises at least one scrubber.

According to a preferred embodiment of the present invention, the separation zone according to (v) consists of the at least one scrubber, preferably of one scrubber. This design is sufficient in order to enable a weight ratio propene to propane in the bottoms stream S3 obtained in (v), i.e. a purity in the range of 1:1 to 100:1, preferably in the range of 5:1 to 50:1, more preferably in the range of 10:1 to 40:1, more preferably in the range of 15:1 to 30:1.

Distillation Unit (v.i)

According to another preferred embodiment of the present invention, the separation zone according to (v) additionally comprises at least one distillation unit, preferably one distillation unit, preferably downstream of the scrubber.

According to a preferred embodiment, the separation zone in (v) comprises the distillation unit and the scrubber, wherein (v.i) propane is separated from the gaseous stream S1 by distillation in the distillation unit comprised in the separation zone, obtaining a gaseous stream S1a, preferably as top stream, which is enriched in propene compared to the stream S1 subjected to distillation conditions, a gaseous stream S1b, preferably as side stream, which is enriched in propene compared to the stream S1 subjected to distillation conditions, and a bottoms stream S1c, which is depleted of propene compared to the stream S1 subjected to distillation conditions; and (v.ii) subjecting the gaseous stream S1a obtained in (v.i) to washing conditions in the scrubber comprised in the separation zone, wherein a solvent mixture comprising organic solvent and water is added as entraining agent, obtaining the bottoms stream S3, which comprises organic solvent, water and at least 70 weight-% of the propene comprised in S1; and the gaseous top stream S4, which comprises at least 5 weight-% of the propane comprised in stream S1.

Preferably, according to this preferred embodiment of the present invention, the separation zone according to (v) consists of the distillation unit (v.i) and the scrubber (v.ii).

As mentioned in more detail above, the preferred organic solvents used in the entraining agent are methanol and acetonitrile. Thus, a first preferred embodiment relates to a process comprising:

(i) providing a stream comprising propene, propane, hydrogen peroxide or a source of hydrogen peroxide, water, and acetonitrile;

(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and acetonitrile;

(iii) removing an effluent stream from the epoxidation zone, the effluent stream comprising propene, propane, propylene oxide, water, and acetonitrile;

(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;

(v) separating propane from the stream S1 in a separation zone, wherein the separation zone in (v) comprises a distillation unit and the scrubber, wherein (v.i) propane is separated from the gaseous stream S1 by distillation in the distillation unit comprised in the separation zone, obtaining a gaseous stream S1a, preferably as top stream, which is enriched in propene compared to the stream S1 subjected to distillation conditions, a gaseous stream S1b, preferably as side stream, which is enriched in propene compared to the stream S1 subjected to distillation conditions, and a bottoms stream S1c, which is depleted of propene compared to the stream S1 subjected to distillation conditions; and (v.ii) subjecting the gaseous stream S1a obtained in (v.i) to washing conditions in the scrubber comprised in the separation zone, wherein a solvent mixture comprising acetonitrile and water is added as entraining agent, obtaining the bottoms stream S3, which comprises acetonitrile, water and at least 70 weight-% of the propene comprised in S1; and the gaseous top stream S4, which comprises at least 5 weight-% of the propane comprised in stream S1.

A second preferred embodiment relates to a process comprising:

(i) providing a stream comprising propene, propane, hydrogen peroxide or a source of hydrogen peroxide, water, and methanol;

(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and methanol;

(iii) removing an effluent stream from the epoxidation zone, the effluent stream comprising propene, propane, propylene oxide, water, and methanol;

(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and methanol compared to the effluent stream subjected to distillation conditions;

(v) separating propane from the stream S1 in a separation zone, wherein the separation zone in (v) comprises a distillation unit and the scrubber, wherein (v.i) propane is separated from the gaseous stream S1 by distillation in the distillation unit comprised in the separation zone, obtaining a gaseous stream S1a, preferably as top stream, which is enriched in propene compared to the stream S1 subjected to distillation conditions, a gaseous stream S1b, preferably as side stream, which is enriched in propene compared to the stream S1 subjected to distillation conditions, and a bottoms stream S1c, which is depleted of propene compared to the stream S1 subjected to distillation conditions; and (v.ii) subjecting the gaseous stream S1a obtained in (v.i) to washing conditions in the scrubber comprised in the separation zone, wherein a solvent mixture comprising methanol and water is added as entraining agent, obtaining the bottoms stream S3, which comprises methanol, water and at least 70 weight-% of the propene comprised in S1; and the gaseous top stream S4, which comprises at least 5 weight-% of the propane comprised in stream S1.

Epoxidation Zone

According to (ii), the feed stream provided in (i) is subjected to epoxidation reaction conditions in an epoxidation zone, wherein a reaction mixture comprising propene, propane, propylene oxide, water and the organic solvent is obtained.

Generally, there are no specific restrictions regarding the design of the epoxidation zone provided that it is suitable for carrying out a, preferably continuous, epoxidation reaction.

Preferably, the epoxidation zone according to (ii) comprises a first epoxidation subzone consisting of one or more epoxidation reactors A. The term "first epoxidation subzone" as used in this context of the present invention relates to the epoxidation subzone into which the feed stream provided in (i) is passed, wherein the epoxidation zone of (ii) may comprise further epoxidation subzones which are arranged downstream of the first epoxidation subzone. If the first epoxidation subzone consisting of two or more epoxidation reactors A, it is preferred that the two or more epoxidation reactors A are arranged in parallel. In this case, it is preferred that in (ii), the feed stream provided in (i) is passed into at least one of the epoxidation reactors A. It is possible, for example, that, while the feed stream provided in (i) is passed into at least one of the epoxidation reactors A, at least one of the reactors A is taken out of operation, for example for maintenance purposes and/or for regenerating the catalyst comprised in the at least one of the reactors A. If the first epoxidation subzone comprises two or more epoxidation reactors A, the reactors in operation are operated essentially identically so that in every epoxidation reactor A in operation, a given epoxidation condition is in the same range in every reactor.

The epoxidation conditions according to (ii) comprise an epoxidation temperature $T^N$, wherein $T^N$ is the temperature of a heat transfer medium used for adjusting the temperature of the reaction mixture in the first epoxidation reaction subzone according to (ii) wherein it is preferred that said temperature is adjusted by passing the heat transfer medium through a jacket of the one or more epoxidation reactors A, wherein $T^N$ is preferably the temperature of the heat transfer medium prior to adjusting the temperature of the reaction mixture, preferably the temperature of the heat transfer medium at the entrance of the jacket of the one or more epoxidation reactors A. If the first epoxidation subzone comprises two or more epoxidation reactors A, the epoxidation temperature $T^N$ relates to the epoxidation temperature $T^N$ of a given reactor A in operation of first epoxidation subzone.

Preferably, the epoxidation conditions according to (ii) comprise a first epoxidation reaction pressure in the range of from 14 to 100 bar, more preferably in the range of from 15 to 32 bar, more preferably in the range of from 15 to 25 bar. The first epoxidation reaction pressure is defined as the absolute pressure at the exit of the first epoxidation subzone. If the first epoxidation subzone comprises two or more epoxidation reactors A, the first epoxidation reaction pressure relates to the absolute pressures at the exit of a given reactor A in operation of first epoxidation subzone.

Preferably, the epoxidation conditions according to (ii) comprise a catalyst loading in the first epoxidation subzone in the range of from 0.05 to 1.25 $h^{-1}$, preferably in the range of from 0.1 to 1 h$^{-1}$, more preferably in the range of from 0.2 to 0.7 h$^{-1}$, wherein the catalyst loading is defined as the ratio of the mass flow rate in kg/h of hydrogen peroxide contained in liquid feed stream provided in (i) relative to the amount in kg of catalyst comprising a titanium zeolite comprised in the first epoxidation subzone according to (ii).

According to a first preferred embodiment of the present invention, the epoxidation zone according to (ii) consists of the first epoxidation subzone.

According to a second preferred embodiment of the present invention, the epoxidation zone according to (ii) additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone. In this case, it is preferred that in (ii), the effluent stream obtained from the first epoxidation subzone, optionally after a suitable intermediate treatment, is passed into at least one of the epoxidation reactors B. It is possible, for example, that, while the effluent stream obtained from the first epoxidation subzone, optionally after a suitable intermediate treatment, is passed into at least one of the epoxidation reactors B, at least one of the reactors B is taken out of operation, for example for maintenance purposes and/or for regenerating the catalyst comprised in the at least one of the reactors B. If the second epoxidation subzone comprises two or more epoxidation reactors B, the reactors in operation are operated essentially identically so that in every epoxidation reactor B in operation, a given epoxidation condition is in the same range in every reactor. Generally, it is conceivable that in addition to the first epoxidation subzone and the second epoxidation subzone, the epoxidation zone according to (ii) comprises at least one further epoxidation subzone arranged downstream of the second epoxidation subzone. Preferably, according to the second preferred embodiment of the present invention, the epoxidation zone according to (ii) consists of the first epoxidation subzone and the second epoxidation subzone.

Preferably, the epoxidation conditions according to (ii) comprise a second epoxidation reaction pressure in the range of from 14 to 100 bar, preferably in the range of from 14.5 to 32 bar, more preferably in the range of from 15 to 25 bar. The second epoxidation reaction pressure is defined as the absolute pressure at the exit of the second epoxidation subzone. If the second epoxidation subzone comprises two or more epoxidation reactors B, the second epoxidation reaction pressure relates to the absolute pressures at the exit of a given reactor B in operation of second epoxidation subzone.

Preferably, the epoxidation conditions according to (ii) comprise an epoxidation catalyst loading in the second epoxidation subzone in the range of from 0.001 to 0.5 h$^{-1}$, more preferably in the range of from 0.005 to 0.3 h$^{-1}$, more preferably in the range of from 0.01 to 0.2 h$^{-1}$, wherein the epoxidation catalyst loading is defined as the ratio of the mass flow rate in kg/h of hydrogen peroxide contained in the feed stream passed into the second epoxidation subzone relative to the amount in kg of epoxidation catalyst comprising a titanium zeolite comprised in the second epoxidation subzone according to (ii).

Preferably, the temperature of the reaction mixture in the second epoxidation reaction subzone is not adjusted by passing a heat transfer medium through a jacket of the one or more epoxidation reactors B. More preferably, the second epoxidation subzone is an essentially adiabatic epoxidation subzone. More preferably, the second epoxidation subzone is an adiabatic epoxidation subzone.

Intermediate Separation

According to a preferred embodiment, the epoxidation zone according to (ii) consists of two epoxidation subzones, wherein a stream from a first epoxidation subzone is separated by distillation into a stream containing non-reacted hydrogen peroxide and a stream comprising propene, propane, propylene oxide, water, and the organic solvent; wherein the stream containing non-reacted hydrogen peroxide is passed into a second epoxidation subzone and the stream comprising propene, propane, propylene oxide, water, and organic solvent from the first epoxidation subzone and/or a stream comprising propene, propane, propylene oxide, water, and the organic solvent from the second epoxidation subzone form the effluent stream comprising propene, propane, propylene oxide, water, and the organic solvent represents the effluent stream according to (iii).

Thus, a further preferred embodiment relates to a process comprising:
  (i) providing a stream comprising propene, propane, hydrogen peroxide or a source of hydrogen peroxide, water, and methanol;
  (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and methanol;
  (iii) removing an effluent stream from the epoxidation zone, the effluent stream comprising propene, propane, propylene oxide, water, and methanol;
  (iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and methanol compared to the effluent stream subjected to distillation conditions;
  (v) separating propane from the stream S1 in a separation zone, wherein the separation zone in (v) comprises a distillation unit and the scrubber, wherein
    (v.i) propane is separated from the gaseous stream S1 by distillation in the distillation unit comprised in the separation zone, obtaining a gaseous stream S1$a$, preferably as top stream, which is enriched in propene compared to the stream S1 subjected to distillation conditions, a gaseous stream S1$b$, preferably as side stream, which is enriched in propene compared to the stream S1 subjected to distillation conditions, and a bottoms stream S1$c$, which is depleted of propene compared to the stream S1 subjected to distillation conditions; and
    (v.ii) subjecting the gaseous stream S1$a$ obtained in (v.i) to washing conditions in the scrubber comprised in the separation zone, wherein a solvent mixture comprising methanol and water is added as entraining agent, obtaining the bottoms stream S3, which comprises methanol, water and at least 70 weight-% of the propene comprised in S1; and the gaseous top stream S4, which comprises at least 5 weight-% of the propane comprised in stream S1;
wherein the epoxidation zone according to (ii) consists of two epoxidation subzones, wherein a stream from a first epoxidation subzone is separated by distillation into a stream containing non-reacted hydrogen peroxide and a stream comprising propene, propane, propylene oxide, water, and methanol; wherein the stream containing non-reacted hydrogen peroxide is passed into a second epoxidation subzone and the stream comprising propene, propane, propylene oxide, water, and methanol from the first epoxidation subzone and/or a stream comprising propene, propane, propylene oxide, water, and methanol from the second epoxidation subzone form the effluent stream according to (iii) comprising propene, propane, propylene oxide, water, and methanol.

Initial Stream Provided in (i)

According to (i), a stream is provided comprising propene, propane, hydrogen peroxide or a source of hydrogen peroxide, water, and an organic solvent. Generally, the stream comprising propene, propane, hydrogen peroxide or a source of hydrogen peroxide, water, and an organic solvent can be provided in (i) according to any conceivable method. Preferably, the stream provided according to (i) comprising propene, propane, hydrogen peroxide or a source of hydrogen peroxide, water, and an organic solvent is prepared from two or more streams. More preferably, the stream is provided in (i) by combining at least three individual streams wherein a first stream comprises hydrogen peroxide or a source of hydrogen peroxide, a second stream comprises propene and propane and a third stream comprises the organic solvent and optionally water.

Preferably,—as described already above—the stream comprising propene additionally comprises propane wherein preferably at least 98 weight-%, more preferably at least 99 weight-%, more preferably at least 99.5 weight-%, more preferably at least 99.9 weight-% of the stream consist of propene and propane. Preferably, the weight ratio of propene relative to propane in the stream is at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. Preferably, a stream is employed having a propene content in the range of from 99 to 99.8 weight-% and a propane content in the range of from 0.2 to 1 weight-%.

The stream comprising hydrogen peroxide can be prepared according to every conceivable method. It is conceivable to obtain the stream comprising hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is then recycled. The preparation of hydrogen peroxide from the elements is also conceivable. Depending on the specific preparation method, the stream comprising hydrogen peroxide can be, for example, an aqueous or an aqueous/methanolic hydrogen peroxide stream, preferably an aqueous hydrogen peroxide stream. In case an aqueous hydrogen peroxide feed is employed, the content of the stream with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. Preferably, at least 25 weight-%, more preferably at least 30 weight-%, more preferably at least 35 weight-% of the stream comprising hydrogen peroxide consist of water and hydrogen peroxide. Preferred ranges are from 30 to 80 weight-% or from 35 to 75 weight-% or from 40 to 70 weight-%.

According to the present invention, it is preferred to employ a stream comprising hydrogen peroxide which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, 5th edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents, whereby preferably none of the solvents is a nitrogen containing substance. This solution of the anthraquinone is usually referred to as the working solution. In this process, the hydrogen peroxide formed in the course of the anthraquinone process is generally separated by extraction from the respective working solution after a hydrogenation/re-oxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution. In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as hydrogen peroxide feed. The production of a crude solution is described, for example, in European patent application EP 1 122 249 A1. As to the term "essentially pure water", reference is made to paragraph 10, page 3 of EP 1 122 249 A1 which is incorporated by reference. The hydrogen peroxide can also be treated to remove trace metals, for example, as described in the WO 2015/049327 A1 before use.

It is conceivable that the hydrogen peroxide is prepared in situ in the epoxidation zone from hydrogen and oxygen, preferably in the presence of a suitable noble metal catalyst comprised in the epoxidation zone according to (ii). A suitable noble metal catalyst preferably comprises one or more of palladium, platinum, silver, gold, rhodium, iridium, ruthenium and osmium. Preferably, the noble metal catalyst comprises palladium. The noble metal catalyst is preferably supported on a carrier, wherein the carrier preferably comprises one or more of $SiO_2$, $Al_2O_3$, $B_2O_3$, $GeO_2$, $Ga_2O_3$, $ZrO_2$, $TiO_2$, MgO, carbon and one or more zeolites, preferably one or more titanium zeolites. More preferably, the carrier comprises the epoxidation catalyst comprising a titanium zeolite. If hydrogen peroxide is prepared in the epoxidation zone according to (ii) in situ from hydrogen and oxygen, the stream provided in (i) comprises propene and preferably propane, hydrogen, oxygen, water, and organic solvent.

Additions to the Effluent Stream and Epoxidation Catalyst

Preferably, the stream provided in (i), optionally the reaction mixture obtained in (ii) and optionally the effluent stream removed in (iii) additionally comprise at least one potassium salt, wherein the at least one potassium salt is selected from the group consisting of at least one inorganic potassium salt, at least one organic potassium salt, and combinations of at least one inorganic potassium salt and at least one organic potassium salt.

Preferably, the at least one potassium salt is selected from the group consisting of at least one inorganic potassium salt selected from the group consisting of potassium hydroxide, potassium halides, potassium nitrate, potassium sulfate, potassium hydrogen sulfate, potassium perchlorate, potassium salts of a phosphorus oxyacid, at least one organic potassium salt selected from the group consisting of potassium salts of aliphatic saturated monocarboxylic acids preferably having 1, 2, 3, 4, 5 or 6 carbon atoms, potassium carbonate, and potassium hydrogen carbonate, and a combination of at least one of the at least one inorganic potassium salts and at least one of the at least one organic potassium salts.

More preferably, the at least one potassium salt is selected from the group consisting of at least one inorganic potassium salt selected from the group consisting of potassium hydroxide, potassium chloride, potassium nitrate, potassium hydrogen phosphate, potassium dihydrogen phosphate, at least one organic potassium salt selected from the group consisting of potassium formate, potassium acetate, potassium carbonate, and potassium hydrogen carbonate, and a combination of at least one of the at least one inorganic potassium salts and at least one of the at least one organic potassium salts. More preferably, the at least one potassium salt comprises at least one of potassium dihydrogen phosphate, dipotassium hydrogen phosphate, and potassium formate.

Preferably, the stream comprising propene, propane, hydrogen peroxide or a source of hydrogen peroxide, water, and an organic solvent and optionally at least one potassium salt provided in (i) is liquid.

Epoxidation Catalyst

According to (ii), the liquid feed stream provided in (i) is passed into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and the organic solvent.

Preferably, titanium zeolite comprised in the epoxidation catalyst is a titanium zeolite having ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON framework structure or a mixed structure of two or more of these framework structures, preferably a titanium zeolite having an MFI framework structure, an MEL framework structure, an MWW framework structure, an ITQ framework structure, a BEA framework structure, a MOR framework structure, or a mixed structure of two or more of these framework structures, preferably an MFI framework structure, or an MWW framework structure.

The epoxidation catalyst comprising a titanium zeolite can be employed in every conceivable form, including a powder, a micropowder, preferably a spray-powder, as a molding comprising a powder, or as a molding comprising a micropowder, preferably a spray-powder. Preferably, the catalyst comprising the titanium zeolite is employed as a molding comprising a powder or a micropowder, preferably a spray-powder, more preferably as a molding comprising a micropowder, preferably a spray-powder. More preferably, the catalyst comprising the titanium zeolite is present in the epoxidation zone as a molding, preferably as fluidized-bed catalyst or a fixed-bed catalyst, more preferably as a fixed-bed catalyst.

In a first preferred embodiment, the titanium zeolite comprised in the epoxidation catalyst is a titanium zeolite having an MFI framework structure, preferably TS-1. Preferably, the titanium zeolite comprised in the epoxidation catalyst is a titanium zeolite having framework type MFI, preferably TS-1, the epoxidation solvent comprises methanol and the stream provided in (i), optionally the reaction mixture obtained in (ii) and optionally the effluent stream removed in (iii) preferably comprise at least one potassium salt, preferably at least one inorganic potassium salt, which preferably comprises at least one of potassium dihydrogen phosphate or dipotassium hydrogen phosphate.

According to this first embodiment, the present invention also relates to a process comprising (i) providing a stream comprising propene, propane, hydrogen peroxide or a source of hydrogen peroxide, water, and methanol;

(ii) passing the liquid feed stream provided in (i) into an epoxidation zone comprising an epoxidation catalyst comprising a titanium zeolite having framework type MFI, preferably TS-1, and subjecting the liquid feed stream to epoxidation reaction conditions in the epoxidation zone, obtaining a reaction mixture comprising propene, propane, propylene oxide, water, and methanol;

(iii) removing an effluent stream from the epoxidation zone, the effluent stream comprising propene, propane, propylene oxide, water, and methanol;

(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and methanol compared to the effluent stream subjected to distillation conditions;

(v) separating propane from the stream S1, comprising subjecting the stream S1 to washing conditions in a scrubber, wherein a solvent mixture comprising methanol and water is added as entraining agent, obtaining a bottoms stream S3, which comprises methanol, water and at least 70 weight-% of the propene comprised in S1; and a gaseous top stream S4, which comprises at least 5 weight-% of the propane comprised in stream S1;

wherein the stream provided in (i), optionally the reaction mixture obtained in (ii) and optionally the effluent stream removed in (iii) preferably comprise at least one potassium salt, preferably at least one inorganic potassium salt, which preferably comprises at least one of potassium dihydrogen phosphate or dipotassium hydrogen phosphate, more preferably at least dipotassium hydrogen phosphate.

In a second preferred embodiment, the titanium zeolite comprised in the epoxidation catalyst is a titanium zeolite having MWW framework structure, which preferably comprises at least one of Al, B, Zr, V, Nb, Ta, Cr, Mo, W, Mn, Fe, Co, Ni, Zn, Ga, Ge, In, Sn, Pb, Pd, Pt, Au, preferably at least one of B, Zr, V, Nb, Ta, Cr, Mo, W, Mn, Fe, Co, Ni, Zn, Ga, Ge, In, Sn, Pb, Pd, Pt, Au, more preferably Zn.

Preferably, the titanium zeolite is an aluminum-free zeolitic material of MWW framework structure, containing titanium, preferably in an amount of from 0.5 to 5 weight-%, more preferably from 1 to 2 weight-%, calculated as elemental titanium and based on the total weight of the titanium containing zeolite, and containing zinc, preferably in an amount of from 0.5 to 5 weight-%, preferably from 1 to 2 weight-%, calculated as elemental zinc and based on the total weight of the titanium containing zeolite. The term "aluminum-free" in the context of the present invention refers to an embodiment according to which the aluminum content of the zeolitic material is 0.05 weight-ppm at most, preferably 0.03 weight-ppm at most, more preferably 0.02 weight-ppm at most, based on the total weight of zeolitic material. The weight-%-values refer to an embodiment according to which the zeolitic material is in dry state, preferably after drying for at least ten hours at 80° C. at a pressure of less than 1013.25 hPa.

More preferably, the titanium zeolite comprised in the epoxidation catalyst is a titanium zeolite of MWW framework structure, preferably being aluminum-free and comprising zinc, the organic solvent comprises acetonitrile and the stream provided in (i), optionally the reaction mixture obtained in (ii) and optionally the effluent stream removed in (iii) preferably comprise at least one potassium salt, preferably at least one organic potassium salt, which preferably comprises at least potassium formate.

According to this second preferred embodiment, the present invention also relates to a process comprising
(i) providing a stream comprising propene, propane, hydrogen peroxide or a source of hydrogen peroxide, water, and acetonitrile;
(ii) passing the liquid feed stream provided in (i) into an epoxidation zone comprising an epoxidation catalyst comprising a titanium zeolite of MWW framework structure, preferably being aluminum-free and comprising zinc, and subjecting the liquid feed stream to epoxidation reaction conditions in the epoxidation zone, obtaining a reaction mixture comprising propene, propane, propylene oxide, water, and acetonitrile;
(iii) removing an effluent stream from the epoxidation zone, the effluent stream comprising propene, propane, propylene oxide, water, and acetonitrile;
(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;
(v) separating propane from the stream S1 in a separation zone, comprising subjecting the stream S1 to washing conditions in a scrubber, wherein a solvent mixture comprising acetonitrile and water is added as entraining agent, obtaining a bottoms stream S3, which comprises acetonitrile, water and at least 70 weight-% of the propene comprised in S1; and a gaseous top stream S4, which comprises at least 5 weight-% of the propane comprised in stream S1;

wherein the stream provided in (i), optionally the reaction mixture obtained in (ii) and optionally the effluent stream removed in (iii) preferably comprise at least one potassium salt, preferably at least one organic potassium salt, which preferably comprises at least potassium formate.

More preferably, the present invention also relates to a process comprising
(i) providing a stream comprising propene, propane, hydrogen peroxide or a source of hydrogen peroxide, water, and acetonitrile;
(ii) passing the liquid feed stream provided in (i) into an epoxidation zone comprising an epoxidation catalyst comprising a titanium zeolite of MWW framework structure, preferably being aluminum-free and comprising zinc, and subjecting the liquid feed stream to epoxidation reaction conditions in the epoxidation zone, obtaining a reaction mixture comprising propene, propane, propylene oxide, water, and acetonitrile;
(iii) removing an effluent stream from the epoxidation zone, the effluent stream comprising propene, propane, propylene oxide, water, and acetonitrile;
(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;
(v) separating propane from the stream S1 in a separation zone, wherein the separation zone in (v) comprises a distillation unit and the scrubber, wherein
(v.i) propane is separated from the gaseous stream S1 by distillation in the distillation unit, obtaining a gaseous stream S1a, preferably as top stream, which is enriched in propene compared to the stream S1 subjected to distillation conditions, a gaseous stream S1b, preferably as side stream, which is enriched in propene compared to the stream S1 subjected to distillation conditions, and a bottoms stream S1c, which is depleted of propene compared to the stream S1 subjected to distillation conditions; and
(v.ii) subjecting the gaseous stream S1a obtained in (v.i) to washing conditions in the scrubber, wherein a solvent mixture comprising organic solvent and water is added as entraining agent, obtaining the bottoms stream S3, which comprises organic solvent, water and at least 70 weight-% of the propene comprised in S1; and the gaseous top stream S4, which comprises at least 5 weight-% of the propane comprised in stream S1;

wherein the stream provided in (i), optionally the reaction mixture obtained in (ii) and optionally the effluent stream removed in (iii) preferably comprise at least one potassium salt, preferably at least one organic potassium salt, which preferably comprises at least potassium formate.

The process for preparing propylene oxide, especially the providing of a stream comprising propene, hydrogen peroxide or a source of hydrogen peroxide, water, and an organic solvent in (i), the passing of the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and the organic solvent, is a continuous process. The present invention is further illustrated by the following embodiments and combinations of embodiments as indicated by the respective dependencies and back-references. In particular, it is noted that in each instance where a range of embodiments is mentioned, for example in the context of a term such as "The process of any of embodiments 1 to 4", every embodiment in this range is meant to be explicitly disclosed for the skilled person, i.e. the wording of this term is to be understood by the skilled person as being synonymous to "The process of any of embodiments 1, 2, 3, and 4".

1. A process for preparing propylene oxide, comprising
   (i) providing a stream comprising propene, propane, hydrogen peroxide or a source of hydrogen peroxide, water, and an organic solvent;
   (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and the organic solvent;
   (iii) removing an effluent stream from the epoxidation zone, the effluent stream comprising propene, propane, propylene oxide, water, and the organic solvent;
   (iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and organic solvent compared to the effluent stream subjected to distillation conditions;
   (v) separating propane from the stream S1 in a separation zone, comprising subjecting the stream S1 to washing conditions in a scrubber, wherein a solvent mixture comprising organic solvent and water is added as entraining agent, obtaining a bottoms stream S3, which comprises organic solvent, water and at least 70 weight-% of the propene comprised in S1; and a gaseous top stream S4, which comprises at least 5 weight-% of the propane comprised in stream S1.

2. The process of embodiment 1, wherein the solvent mixture comprising organic solvent and water added as entraining agent in (v) has a capacity KAP with regard to propene at 25° C. in the range from 0.01 to 0.2, preferably in the range from 0.02 to 0.19.

3. The process of embodiment 1 or 2, wherein the solvent mixture comprising organic solvent and water added as entraining agent in (v) has a mass based capacity $KAP_m$ with regard to propene at 25° C. in the range from 4.4 to 10, preferably in the range from 4.5 to 9, more preferably in the range from 4.6 to 8, more preferably in the range from 4.7 to 7.

4. The process of any of embodiments 1 to 3, wherein the solvent mixture comprising organic solvent and water added as entraining agent in (v) has a selectivity S with regard to propene at 25° C. in the range from 1.3 to 3.5, preferably in the range from 1.4 to 3.4, more preferably in the range from 1.5 to 3.3.

5. The process of any of embodiments 1 to 4, wherein the organic solvent comprised in the solvent mixture used as entraining agent in (v) is selected from the group consisting of acetonitrile, butanone, propanone, cyclopentanone, methylacetate, 1,3-dioxoloane, ethylformate, 1,4-dioxane, 1,3-dioxane, valeronitrile, butyronitrile, methylformate, propionitrile, dimethylcarbonate, dimethylformamide, acetophenone, 1-methoxy-2-propanone, 1-phenyl-2-propanone, 1,1,1-trifluoro-2-propanone, benzonitrile, 2-(2-methoxyethoxy)ethanol, methanol and mixtures of two or more thereof, preferably from acetonitrile, methanol and mixtures of acetonitrile and methanol, more preferably acetonitrile or methanol.

6. The process of any of embodiments 1 to 5, wherein the organic solvent comprised in the solvent mixture is the same organic solvent as comprised in the stream provided in (i).

7. The process of any of embodiments 1 to 6, wherein the solvent mixture used as entraining agent in (v) comprises at least 0.1 weight-%, preferably at least 1 weight-%, more preferably at least 5 weight-%, more preferably at least 10 weight-%, more preferably at least 15 weight-%, of water based on the total weight of the solvent mixture.

8. The process according to any of embodiments 1 to 7, comprising
   (i) providing a stream comprising propene, propane, hydrogen peroxide or a source of hydrogen peroxide, water, and acetonitrile;
   (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and acetonitrile;
   (iii) removing an effluent stream from the epoxidation zone, the effluent stream comprising propene, propane, propylene oxide, water, and acetonitrile;
   (iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;
   (v) separating propane from the stream S1 in a separation zone, comprising subjecting the stream S1 to washing conditions in a scrubber, wherein a solvent mixture comprising acetonitrile and water is added as entraining agent, obtaining a bottoms stream S3, which comprises acetonitrile, water and at least 70 weight-% of the propene comprised in S1; and a gaseous top stream S4, which comprises at least 5 weight-% of the propane comprised in stream S1.

9. The process according to any of embodiments 1 to 7, comprising
   (i) providing a stream comprising propene, propane, hydrogen peroxide or a source of hydrogen peroxide, water, and methanol;

(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and methanol;

(iii) removing an effluent stream from the epoxidation zone, the effluent stream comprising propene, propane, propylene oxide, water, and methanol;

(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and methanol compared to the effluent stream subjected to distillation conditions;

(v) separating propane from the stream S1 in a separation zone, comprising subjecting the stream S1 to washing conditions in a scrubber, wherein a solvent mixture comprising methanol and water is added as entraining agent, obtaining a bottoms stream S3, which comprises methanol, water and at least 70 weight-% of the propene comprised in S1; and a gaseous top stream S4, which comprises at least 5 weight-% of the propane comprised in stream S1.

10. The process of any of embodiments 1 to 9, wherein the scrubber employed in (v) is a column, preferably having from 2 to 20, more preferably from 3 to 18, more preferably from 5 to 15, theoretical trays.

11. The process of any of embodiments 1 to 10, wherein the solvent mixture comprising organic solvent and water added as entraining agent to the scrubber employed in (v) is added at a theoretical tray above the feed tray of the stream S1, preferably at a tray in the range of tray 1 to 10, more preferably in the range of tray 1 to 5, more preferably in the range of tray 1 to 3, counted from the top, more preferably at the top of the scrubber (tray 1).

12. The process of any of embodiments 1 to 11, wherein the weight ratio of solvent mixture comprising organic solvent and water added as entraining agent to the scrubber employed in (v) per hour to the weight ratio of stream S1 feed to the scrubber per hour is in the range of 1:10 to 10:1, preferably in the range of 1:1 to 10:1, more preferably in the range of 2:1 to 5:1.

13. The process of any of embodiments 1 to 12, wherein the scrubber is operated at a top temperature in the range of 10 to 30° C., preferably in the range of 14 to 26° C., more preferably in the range of 15 to 22° C.

14. The process of any of embodiments 1 to 13, wherein the scrubber employed in (v) is operated at a sump temperature in the range of 20 to 65° C., preferably in the range of 25 to 60° C., more preferably in the range of 27 to 50° C.

15. The process of any of embodiments 1 to 14, wherein the scrubber employed in (v) is operated at a sump pressure of in the range of 1 to 35 bar, preferably in the range of 5 to 32 bar, more preferably in the range of 10 to 30 bar.

16. The process of any of embodiments 1 to 15, wherein at least 95 weight-%, preferably from 95 to 99.6 weight-%, more preferably from 98 to 99.7 weight-%, more preferably from 99 to 99.8 weight-%, of the effluent stream removed in (iii) consist of propylene oxide, the organic solvent, water, propene, oxygen, and propane.

17. The process of any of embodiments 1 to 16, wherein the effluent stream removed in (iii) comprises the propylene oxide in an amount of from 5 to 20 weight-%, preferably from 6 to 18 weight-%, more preferably from 7 to 14 weight-%, based on the total weight of the effluent stream; the organic solvent in an amount of from 55 to 75 weight-%, preferably from 6 to 74 weight-%, based on the total weight of the effluent stream; the water in an amount of from 10 to 25 weight-%, preferably from 15 to 20 weight-%, based on the total weight of the effluent stream; the propene in an amount of from 1 to 5 weight-%, preferably from 3 to 4.5 weight-%, based on the total weight of the effluent stream; oxygen in an amount of from 0.05 to 1 weight-%, preferably from 0.1 to 0.5 weight-%, based on the total weight of the effluent stream; and the propane in an amount of from 0.1 to 2 weight-%, preferably from 0.2 to 1 weight-%, based on the total weight of the effluent stream.

18. The process of any of embodiments 1 to 17, wherein at least 90 weight-%, preferably from 90 to 96 weight-%, more preferably from 92 to 97 weight-%, more preferably from 95 to 98 weight-% of the gaseous stream S1 obtained in (iv) consist of propene and propane.

19. The process of any of embodiments 1 to 18, wherein the weight ratio propene to propane in the gaseous stream S1 obtained in (iv) is in the range of 5:1 to 100:1, preferably in the range of 6:1 to 80:1, more preferably in the range of 7:1 to 50:1.

20. The process of any of embodiments 1 to 19, wherein the gaseous stream S1 obtained in (iv) comprises the propene in an amount of from 85 to 95 weight-%, preferably from 87 to 94 weight-%, more preferably from 90 to 93 weight-%, based on the total weight of the stream S1; the propane in an amount of from 1 to 10 weight-%, preferably from 3 to 7 weight-%, more preferably from 4 to 6 weight-%, based on the total weight of the stream S1, water in an amount of from 0 to 1 weight-% based on the total weight of the stream S1, and nitrogen in an amount of from 0.1 to 5 weight-% based on the total weight of the stream S1.

21. The process of any of embodiments 1 to 20, wherein at least 90 weight-%, preferably from 90 to 96 weight-%, more preferably from 92 to 97 weight-%, more preferably from 95 to 98 weight-% of the liquid bottoms stream S2 obtained in (iv) consists of propylene oxide, water and organic solvent.

22. The process of any of embodiments 1 to 21, wherein at least 90 weight-%, preferably from 90 to 98 weight-%, more preferably from 92 to 98.5 weight-%, more preferably from 95 to 99 weight-% of the bottoms stream S3 obtained in (v) consists of organic solvent, water, propene and propane, CO and $CO_2$.

23. The process of any of embodiments 1 to 22, wherein the bottoms stream S3 obtained in (v) comprises at least 75 weight-%, preferably at least 80 weight-%, more preferably at least 90 weight-%, more preferably at least 95 weight-%, of the propene comprised in S1.

24. The process of any of embodiments 1 to 23, wherein the weight ratio propene to propane in the bottoms stream S3 obtained in (v) is in the range of 1:1 to 100:1, preferably in the range of 5:1 to 50:1, more preferably in the range of 10:1 to 40:1, more preferably in the range of 15:1 to 30:1.

25. The process of any of embodiments 1 to 24, wherein at the outmost 50 weight-%, preferably 40 weight-%, more preferably 30 weight-%, more preferably 25 weight-% of the gaseous top stream S4 consist of propene and propane.

26. The process of any of embodiments 1 to 25, wherein the gaseous top stream S4 obtained in (v) comprises at the outmost 30 weight-%, preferably at the outmost 25 weight-%, more preferably at the outmost 20 weight-%, more preferably at the outmost 10 weight-%, more preferably at the outmost 5 weight-%, more preferably at the outmost 3 weight-%, of the propene comprised in S1.

27. The process of any of embodiments 1 to 26, wherein the weight ratio propene to propane in the gaseous top stream S4 obtained in (v) is in the range of 1:1 to 15:1, preferably in the range of 2:1 to 14:1, more preferably in the range of 3:1 to 12:1.

28. The process of any of embodiments 1 to 27, wherein prior to (iv), the effluent stream removed according to (iii) is depressurized.

29. The process of embodiment 28, wherein from depressurizing the effluent stream, a gaseous stream and a liquid stream are obtained.

30. The process of embodiment 29, wherein the gaseous and liquid streams are passed separately to the distillation unit employed according to (iv), preferably to the same theoretical tray of the distillation unit employed according to (iv).

31. The process of any of embodiments 1 to 30, wherein the separation zone in (v) comprises a distillation unit and the scrubber, wherein
(v.i) propane is separated from the gaseous stream S1 by distillation in the distillation unit comprised in the separation zone, obtaining a gaseous stream S1a, preferably as top stream, which is enriched in propene compared to the stream S1 subjected to distillation conditions, a gaseous stream S1b, preferably as side stream, which is enriched in propene compared to the stream S1 subjected to distillation conditions, and a bottoms stream S1c, which is depleted of propene compared to the stream S1 subjected to distillation conditions; and
(v.ii) subjecting the gaseous stream S1a obtained in (v.i) to washing conditions in the scrubber comprised in the separation zone, wherein a solvent mixture comprising organic solvent and water is added as entraining agent, obtaining the bottoms stream S3, which comprises organic solvent, water and at least 70 weight-% of the propene comprised in S1; and the gaseous top stream S4, which comprises at least 5 weight-% of the propane comprised in stream S1.

32. The process according to any of embodiments 1 to 31, comprising
(i) providing a stream comprising propene, propane, hydrogen peroxide or a source of hydrogen peroxide, water, and acetonitrile;
(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and acetonitrile;
(iii) removing an effluent stream from the epoxidation zone, the effluent stream comprising propene, propane, propylene oxide, water, and acetonitrile;
(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;
(v) separating propane from the stream S1 in a separation zone, wherein the separation zone in (v) comprises a distillation unit and the scrubber, wherein
(v.i) propane is separated from the gaseous stream S1 by distillation in the distillation unit comprised in the separation zone, obtaining a gaseous stream S1a, preferably as top stream, which is enriched in propene compared to the stream S1 subjected to distillation conditions, a gaseous stream S1b, preferably as side stream, which is enriched in propene compared to the stream S1 subjected to distillation conditions, and a bottoms stream S1c, which is depleted of propene compared to the stream S1 subjected to distillation conditions; and
(v.ii) subjecting the gaseous stream S1a obtained in (v.i) to washing conditions in the scrubber comprised in the separation zone, wherein a solvent mixture comprising acetonitrile and water is added as entraining agent, obtaining the bottoms stream S3, which comprises acetonitrile, water and at least 70 weight-% of the propene comprised in S1; and the gaseous top stream S4, which comprises at least 5 weight-% of the propane comprised in stream S1.

33. The process according to any of embodiments 1 to 31, comprising
(i) providing a stream comprising propene, propane, hydrogen peroxide or a source of hydrogen peroxide, water, and methanol;
(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and methanol;
(iii) removing an effluent stream from the epoxidation zone, the effluent stream comprising propene, propane, propylene oxide, water, and methanol;
(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and methanol compared to the effluent stream subjected to distillation conditions;
(v) separating propane from the stream S1 in a separation zone, wherein the separation zone in (v) comprises a distillation unit and the scrubber, wherein
(v.i) propane is separated from the gaseous stream S1 by distillation in the distillation unit comprised in the separation zone, obtaining a gaseous stream S1a, preferably as top stream, which is enriched in propene compared to the stream S1 subjected to distillation conditions, a gaseous stream S1b, preferably as side stream, which is enriched in propene compared to the stream S1 subjected to distillation conditions, and a bottoms stream S1c, which is depleted of propene compared to the stream S1 subjected to distillation conditions; and
(v.ii) subjecting the gaseous stream S1a obtained in (v.i) to washing conditions in the scrubber comprised in the separation zone, wherein a solvent mixture comprising methanol and water is added as entraining agent, obtaining the bottoms stream S3, which comprises methanol, water and at least 70 weight-% of the propene comprised in S1; and the gaseous top stream S4, which comprises at least 5 weight-% of the propane comprised in stream S1.

34. The process of any of embodiments 1 to 33, wherein the epoxidation zone according to (ii) comprises a first epoxidation subzone consisting of one or more epoxidation reactors A, wherein, if the first epoxidation subzone comprises two or more epoxidation reactors A, the two or more epoxidation reactors A are arranged in parallel, and wherein in (ii), the liquid feed stream provided in (i) is passed into at least one of the epoxidation reactors A.

35. The process of embodiment 34, wherein the epoxidation zone according to (ii) consists of the first epoxidation subzone.

36. The process of embodiment 34 or 35, wherein the epoxidation conditions according to (ii) comprise a first epoxidation reaction pressure in the range of from 14 to 100 bar, preferably in the range of from 15 to 32 bar, more preferably in the range of from 15 to 25 bar, wherein the first epoxidation reaction pressure is defined as the absolute pressure at the exit of the first epoxidation subzone.

37. The process of any of embodiments 34 to 36, wherein the epoxidation conditions according to (ii) comprise a catalyst loading in the first epoxidation subzone in the range of from 0.05 to 1.25 $h^{-1}$, preferably in the range of from 0.1 to 1 $h^{-1}$, more preferably in the range of from 0.2 to 0.7 $h^{-1}$, wherein the catalyst loading is defined as the ratio of the mass flow rate in kg/h of hydrogen peroxide contained in liquid feed stream provided in (i) relative to the amount in kg of catalyst comprising a titanium zeolite comprised in the first epoxidation subzone according to (ii).

38. The process of any of embodiments 34 to 37, wherein the epoxidation zone additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone.

39. The process of any of embodiments 34 to 38, wherein the epoxidation zone according to (ii) consists of the first epoxidation subzone and the second epoxidation subzone.

40. The process of embodiment 38 or 39, wherein the epoxidation zone according to (ii) consists of two epoxidation subzones, wherein a stream from a first epoxidation subzone is separated by distillation into a stream containing non-reacted hydrogen peroxide and a stream comprising propene, propane, propylene oxide, water, and the organic solvent; wherein the stream containing non-reacted hydrogen peroxide is passed into a second epoxidation subzone and the stream comprising propene, propane, propylene oxide, water, and organic solvent from the first epoxidation subzone and/or a stream comprising propene, propane, propylene oxide, water, and the organic solvent from the second epoxidation subzone form the effluent stream comprising propene, propane, propylene oxide, water, and the organic solvent represents the effluent stream according to (iii).

41. The process of any of embodiments 1 to 40, wherein the stream comprising propene, propane, hydrogen peroxide or a source of hydrogen peroxide, water, and an organic solvent provided in (i) is prepared from two or more streams.

42. The process of any of embodiments 1 to 41, wherein the stream provided in (i), optionally the reaction mixture obtained in (ii) and optionally the effluent stream removed in (iii) additionally comprise at least one potassium salt, wherein the at least one potassium salt is selected from the group consisting of at least one inorganic potassium salt, at least one organic potassium salt, and combinations of at least one inorganic potassium salt and at least one organic potassium salt.

43. The process of embodiment 42, wherein the at least one potassium salt is selected from the group consisting of at least one inorganic potassium salt selected from the group consisting of potassium hydroxide, potassium halides, potassium nitrate, potassium sulfate, potassium hydrogen sulfate, potassium perchlorate, potassium salts of a phosphorus oxyacid, at least one organic potassium salt selected from the group consisting of potassium salts of aliphatic saturated monocarboxylic acids preferably having 1, 2, 3, 4, 5 or 6 carbon atoms, potassium carbonate, and potassium hydrogen carbonate, and a combination of at least one of the at least one inorganic potassium salts and at least one of the at least one organic potassium salts.

44. The process of embodiment 42 or 43, wherein the at least one potassium salt is selected from the group consisting of at least one inorganic potassium salt selected from the group consisting of potassium hydroxide, potassium chloride, potassium nitrate, potassium hydrogen phosphate, potassium dihydrogen phosphate, at least one organic potassium salt selected from the group consisting of potassium formate, potassium acetate, potassium carbonate, and potassium hydrogen carbonate, and a combination of at least one of the at least one inorganic potassium salts and at least one of the at least one organic potassium salts.

45. The process of any of embodiments 43 to 44, wherein the at least one potassium salt comprises at least one of potassium dihydrogen phosphate, dipotassium hydrogen phosphate, and potassium formate.

46. The process of any of embodiments 1 to 45, wherein the stream comprising propene, propane, hydrogen peroxide or a source of hydrogen peroxide, water, and an organic solvent and optionally at least one potassium salt provided in (i) is liquid.

47. The process of any of embodiments 1 to 46, wherein the titanium zeolite comprised in the epoxidation catalyst is a titanium zeolite having ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON framework structure or a mixed structure of two or more of these framework structures, preferably a titanium zeolite having an MFI framework structure, an MEL framework structure, an MWW framework structure, an ITQ framework structure, a BEA framework structure, a MOR framework structure, or a mixed structure of two or more of these framework structures, preferably an MFI framework structure, or an MWW framework structure.

48. The process of any of embodiments 1 to 47, wherein the titanium zeolite comprised in the epoxidation catalyst is a titanium zeolite having an MFI framework structure, preferably TS-1.

49. The process of any of embodiments 1 to 48, wherein the titanium zeolite comprised in the epoxidation catalyst is a titanium zeolite having framework type MFI, preferably TS-1, the epoxidation solvent comprises methanol and the stream provided in (i), optionally the reaction mixture obtained in (ii) and optionally the effluent stream removed in (iii) preferably comprise at least one potassium salt, more preferably at least one inorganic potassium salt, which preferably comprises at least one of potassium dihydrogen phosphate or dipotassium hydrogen phosphate.

50. The process according to any of embodiments 1 to 49, comprising
    (i) providing a stream comprising propene, propane, hydrogen peroxide or a source of hydrogen peroxide, water, and methanol;
    (ii) passing the liquid feed stream provided in (i) into an epoxidation zone comprising an epoxidation catalyst comprising a titanium zeolite having framework type MFI, preferably TS-1, and subjecting the liquid feed stream to epoxidation reaction conditions in the epoxidation zone, obtaining a reaction mixture comprising propene, propane, propylene oxide, water, and methanol;
    (iii) removing an effluent stream from the epoxidation zone, the effluent stream comprising propene, propane, propylene oxide, water, and methanol;
    (iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and methanol compared to the effluent stream subjected to distillation conditions;
    (v) separating propane from the stream S1, comprising subjecting the stream S1 to washing conditions in a scrubber, wherein a solvent mixture comprising methanol and water is added as entraining agent, obtaining a bottoms stream S3, which comprises methanol, water and at least 70 weight-% of the propene comprised in S1; and a gaseous top stream S4, which comprises at least 5 weight-% of the propane comprised in stream S1;
    wherein the stream provided in (i), optionally the reaction mixture obtained in (ii) and optionally the effluent stream removed in (iii) preferably comprise at least one potassium salt, preferably at least one inorganic potassium salt, which preferably comprises at least one of potassium dihydrogen phosphate or dipotassium hydrogen phosphate, more preferably at least dipotassium hydrogen phosphate.

51. The process of any of embodiments 1 to 47, wherein the titanium zeolite comprised in the epoxidation catalyst is a titanium zeolite having MWW framework structure, which preferably comprises at least one of Al, B, Zr, V, Nb, Ta, Cr, Mo, W, Mn, Fe, Co, Ni, Zn, Ga, Ge, In, Sn, Pb, Pd, Pt, Au, preferably at least one of B, Zr, V, Nb, Ta, Cr, Mo, W, Mn, Fe, Co, Ni, Zn, Ga, Ge, In, Sn, Pb, Pd, Pt, Au, more preferably Zn.

52. The process of any of embodiments 1 to 47 or 51, wherein the titanium zeolite is an aluminum-free zeolitic material of MWW framework structure, containing titanium, preferably in an amount of from 0.5 to 5 weight-%, more preferably from 1 to 2 weight-%, calculated as elemental titanium and based on the total weight of the titanium containing zeolite, and containing zinc, preferably in an amount of from 0.5 to 5 weight-%, preferably from 1 to 2 weight-%, calculated as elemental zinc and based on the total weight of the titanium containing zeolite.

53. The process of any of embodiments 1 to 47 or 51 to 52, wherein the titanium zeolite comprised in the epoxidation catalyst is a titanium zeolite of MWW framework structure, preferably being aluminum-free and comprising zinc, the organic solvent comprises acetonitrile and the stream provided in (i), optionally the reaction mixture obtained in (ii) and optionally the effluent stream removed in (iii) preferably comprise at least one potassium salt, preferably at least one organic potassium salt, which preferably comprises at least potassium formate.

54. The process according to any of embodiments 1 to 47 or 51 to 53, comprising
    (i) providing a stream comprising propene, propane, hydrogen peroxide or a source of hydrogen peroxide, water, and acetonitrile;
    (ii) passing the liquid feed stream provided in (i) into an epoxidation zone comprising an epoxidation catalyst comprising a titanium zeolite of MWW framework structure, preferably being aluminum-free and comprising zinc, and subjecting the liquid feed stream to epoxidation reaction conditions in the epoxidation zone, obtaining a reaction mixture comprising propene, propane, propylene oxide, water, and acetonitrile;
    (iii) removing an effluent stream from the epoxidation zone, the effluent stream comprising propene, propane, propylene oxide, water, and acetonitrile;
    (iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;
    (v) separating propane from the stream S1 in a separation zone, comprising subjecting the stream S1 to washing conditions in a scrubber, wherein a solvent mixture comprising acetonitrile and water is added as entraining agent, obtaining a bottoms stream S3, which comprises acetonitrile, water and at least 70 weight-% of the propene comprised in S1; and a gaseous top stream S4, which comprises at least 5 weight-% of the propane comprised in stream S1;
    wherein the stream provided in (i), optionally the reaction mixture obtained in (ii) and optionally the effluent stream removed in (iii) preferably comprise at least one potassium salt, preferably at least one organic potassium salt, which preferably comprises at least potassium formate.

55. The process according to embodiment 54, comprising
    (i) providing a stream comprising propene, propane, hydrogen peroxide or a source of hydrogen peroxide, water, and acetonitrile;

(ii) passing the liquid feed stream provided in (i) into an epoxidation zone comprising an epoxidation catalyst comprising a titanium zeolite of MWW framework structure, preferably being aluminum-free and comprising zinc, and subjecting the liquid feed stream to epoxidation reaction conditions in the epoxidation zone, obtaining a reaction mixture comprising propene, propane, propylene oxide, water, and acetonitrile;

(iii) removing an effluent stream from the epoxidation zone, the effluent stream comprising propene, propane, propylene oxide, water, and acetonitrile;

(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;

(v) separating propane from the stream S1 in a separation zone, wherein the separation zone in (v) comprises a distillation unit and the scrubber, wherein (v.i) propane is separated from the gaseous stream S1 by distillation in the distillation unit, obtaining a gaseous stream S1a, preferably as top stream, which is enriched in propene compared to the stream S1 subjected to distillation conditions, a gaseous stream S1b, preferably as side stream, which is enriched in propene compared to the stream S1 subjected to distillation conditions, and a bottoms stream S1c, which is depleted of propene compared to the stream S1 subjected to distillation conditions; and (v.ii) subjecting the gaseous stream S1a obtained in (v.i) to washing conditions in the scrubber, wherein a solvent mixture comprising organic solvent and water is added as entraining agent, obtaining the bottoms stream S3, which comprises organic solvent, water and at least 70 weight-% of the propene comprised in S1; and the gaseous top stream S4, which comprises at least 5 weight-% of the propane comprised in stream S1;

wherein the stream provided in (i), optionally the reaction mixture obtained in (ii) and optionally the effluent stream removed in (iii) preferably comprise at least one potassium salt, preferably at least one organic potassium salt, which preferably comprises at least potassium formate.

56. The process of any of embodiments 1 to 55, which is a continuous process.

The present invention is further illustrated by the following reference examples, comparative examples, and examples.

EXAMPLES

Reference Example 1: Preparation of a TS-1 Catalyst 1.1 Powder Synthesis

| Starting materials: | |
| --- | --- |
| 720 kg | tetraethoxy silane (TEOS) (Wacker, TES-28) |
| 950 kg | tetra-n-propylammonium hydroxide (TPAOH) (40 wt.-% in water, Sachen, USA) |
| 13.5 kg | tetraethoxy titanate (TEOT) (Du Pont, Tyzor ET) |

TEOS (300 kg) were loaded into a stirred tank reactor at room temperature and stirring (100 r.p.m.) was started. In a second vessel, 60 kg TEOS and 13.5 kg TEOT were first mixed and then added to the TEOS in the first vessel. Subsequently, another 360 kg TEOS were added to the mixture in the first vessel. Then, the content of the first vessel was stirred for 10 min before 950 g TPAOH were added. Stirring was continued for 60 min. Ethanol released by hydrolysis was separated by distillation at a bottoms temperature of 95° C. 300 kg water were then added to the content of the first vessel, and water in an amount equivalent to the amount of distillate was further added. The obtained mixture was stirred for 1 h. Crystallization was performed at 175° C. within 12 h at autogenous pressure. The obtained titanium silicalite-1 crystals were separated, dried, and calcined at a temperature of 500° C. in air for 6 h.

1.2 Silica Sol Synthesis

| Starting materials: | |
| --- | --- |
| 1096 kg | distilled water |
| 760 kg | TEOS (Dynasil, Wacker) |
| 2.5 liter | aqueous ammonia solution (25 wt.-%) |

In a vessel, 1096 g water were provided and 2.5 l aqueous ammonia solution were added. The obtained mixture was stirred for 15 min. Subsequently, the content of the vessel was heated to a temperature of 40° C. Then, 360 kg TEOS were added and the content of the vessel was heated to a temperature of 80° C. This temperature was maintained for 2 h (under reflux). Finally, the alcohol obtained by hydrolysis was distilled off by heating the content of the vessel to a temperature of 95° C. After distillation, the content of the vessel was cooled to a temperature of 40° C.

This procedure was repeated 4 times.

1.3 Shaping of a TS-1 Catalyst

| Starting materials | |
| --- | --- |
| 120 kg | TS-1 powder (obtained as described above) |
| 40 kg | Aerosil 200 (Degussa) |
| 176 kg | silica sol obtained as described above (22.5 wt.-% $SiO_2$) |
| 8 kg | Walocel (Wolff, Walsrode, Germany) |
| 4.9 kg | poly(ethylene oxide) (PEO) (Union Carbide, PolyOX Coagulant) |
| 80 liter | distilled water |

TS-1 powder, Aerosil and Walocel were mixed for 20 min in a muller. Then, the silica sol was added. 35 min after the first addition of TS-1, 70 l of distilled water were added. After another 35 min, 2 kg PEO were added. After another 20 min, 10 l water were added. After another 10 min, 2.9 kg PEO were added. The formable mass was extruded through a matrix having circular holes with a diameter of 1.5 mm. The obtained strands were calcined in a band calciner at a temperature of 550° C.

This procedure was repeated four times.

In total, 1740 kg strands were obtained with a bulk density of 470 to 480 g/l. The titanium content of the strands was 0.71 wt.-%, the Si content was 44 wt.-%. The pore volume of the strands, determined via Hg porosimetry, was 73 ml/g.

Reference Example 2: Preparation of a Catalyst Comprising a Titanium Zeolite Having Framework Type MWW 2.1 Preparation of Boron Containing Zeolite of Structure MWW (BMWW)

A 2 $m^3$ stirred tank reactor was first loaded with 470.4 kg of deionized water. After starting the stirrer at 70 rpm, boric acid (162.5 kg) was added and the suspension was stirred for 3 h. Subsequently, piperidine (272.5 kg) was added at once causing the temperature to rise from 28° C. to 46° C. To this solution colloidal silica (Ludox® AS040, 392.0 kg) was added. The reactor was then slowly heated to 170° C. within 5 hours and then kept at this temperature under stirring for 120 hours. The maximum pressure during the reaction was 9.3 bar. Afterwards the reactor was cooled down to 50° C. The gel obtained had a pH of 11.3 and a viscosity of 15 mPa·s at 20° C. The gel was then filtered and the filter cake washed with deionized water until the conductivity of the washings was below 500 microSiemens/cm. The filter cake was then suspended in deionized water and the suspension was spray-dried at 235° C. using nitrogen as the carrier gas. The white powder obtained (174.3 kg) contained 3.5 weight-% water. This white powder was then calcined at 650° C. in a rotary kiln to give 138.2 kg of boron containing zeolite of structure type MWW (BMWW) as a white powder.

2.2 Deboronation of BMWW with Water

A 5 $m^3$ stirred tank reactor was loaded with 125 kg of the BMWW obtained according to the previous step 1.1 and 3750 kg of deionized water. The reactor was then slowly heated to 100° C. within 1 hour under stirring at 70 rpm, and then kept at this temperature for 20 hours and finally cooled to a temperature below 50° C. before it was filtered. The filter cake was then washed with deionized water until the washings had conductivity below 15 microSiemens/cm. The filter cake was then dried for 6 hours under a nitrogen stream. The filter cake was then removed and suspended in 850 kg of deionized water. This suspension was then spray-dried at 235° C. using nitrogen as the carrier gas. The spray dried material weighed 118.5 kg and contained 42.5 weight-% Si, 0.06 weight-% B and 0.23 weight-% C (total organic carbon, TOC).

2.3 Preparation of Titanium Containing Zeolite of Structure Type MWW (TiMWW)

A 2 $m^3$ stirred tank reactor was first loaded with 111.2 kg of the spray-dried material from the previous step 1.2. In a separate 2 $m^3$ stirred tank reactor were placed 400 kg of deionized water. After starting the stirrer at 80 rpm, piperidine (244.0 kg) was added. After the addition of piperidine was finished the mixture was stirred for 5 minutes before tetrabutyl orthotitanate (22.4 kg) was added. The pipe through which the titanate was added was then flushed with 40 kg of deionized water. The mixture was then stirred for 1 hour before being added to the first stirred tank reactor containing the spray-dried powder under stirring (50 rpm). The reactor was then heated to 170° C. and kept at this temperature for 120 h before being cooled to 50° C. The maximum pressure during the reaction was 10.6 bar. The cooled suspension was then filtered and the filter cake was washed with deionized water until the washings had conductivity below 1300 microSiemens/cm and an approximately neutral pH value. The filter cake was then dried under a nitrogen stream for 6 hours. The filter cake containing about 80 weight-% of water was used directly for the next step. The filter cake from the previous step and 1000 kg of deionized water were filled in a 2 $m^3$ stirred tank reactor. Then 1900 kg of nitric acid (53 weight-% in water) were added under stirring at 70 rpm. The reactor was then heated to 100° C. and kept at this temperature for 20 hours before being cooled to 50° C. The suspension obtained was then filtered and the filter cake was washed with deionized water until the conductivity was below 10 microSiemens/cm and the washings were approximately neutral. Subsequently the filter cake was dried under a stream of nitrogen for 6 hours. This filter cake was then suspended in water and spray-dried at 235° C. using nitrogen as the carrier gas. 96 kg of a spray-dried powder were obtained. This material was then calcined in a rotary kiln at 650° C. 84 kg of titanium zeolite of structure type MWW (TiMWW) were obtained as a powder containing 43 weight-% Si, 2.0 weight-% Ti and 0.2 weight-% C (TOC). The pore volume determined by Hg-porosimetry according to DIN 66133 was 7.3 ml/g and the BET surface area determined according to DIN 66131 was 467 m 2/g.

2.4 Preparation of a Zinc Containing TiMWW (Zn-TiMWW) by Impregnation a) In a vessel equipped with a reflux condenser, a solution of 981 kg deionized water and 6.0 kg zinc acetate dihydrate was prepared within 30 min. Under stirring (40 r.p.m.), 32.7 kg of the calcined Ti-MWW material obtained according to 1.3 above were suspended. Subsequently, the vessel was closed and the reflux condenser put into operation. The stirring rate was increased to 70 r.p.m.

b) In a vessel equipped with a reflux condenser, a solution of 585 kg deionized water and 3.58 kg zinc acetate dihydrate was prepared within 30 min. Under stirring (40 r.p.m.), 19.5 kg of the calcined Ti-MWW material obtained according to 1.3 above were suspended. Subsequently, the vessel was closed and the reflux condenser put into operation. The stirring rate was increased to 70 r.p.m.

In all batches a) and b), the mixture in the vessel was heated to 100° C. within 1 h and kept under reflux for 2 h at a stirring rate of 70 r.p.m. Then, the mixture was cooled within 2 h to a temperature of less than 50° C. For each batch a) and b), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h. In total 297 kg of nitrogen dried filter cake were obtained. The thus dried Zn-impregnated TiMWW material (ZnTiMWW), had a Si content of 42 weight-%, a Ti content of 1.8 weight-%, a Zn content of 1.3 weight-.%.

From 297 kg of the mixture of the filter cake obtained above, an aqueous suspension was prepared with deionized water, the suspension having a solid content of 15 weight-%. This suspension was subjected to spray-drying in a spray-tower with the following spray-drying conditions:

apparatus used: spray tower with one nozzle
operation mode: nitrogen straight
configuration: dehumidifier-filter-scrubber
dosage: flexible-tube pump VF 10 (supplier: Verder)
nozzle with a diameter of 4 mm (supplier: Niro)
filter material: Nomex® needle-felt 10 $m^2$

| Runtime/h | | 0.5 | 1.5 | 2.5 | 3.5 | 4.5 |
|---|---|---|---|---|---|---|
| Flow rate gas/(kg/h) | | 550 | 550 | 550 | 550 | 550 |
| Temperature drying gas/° C. | spray tower (in) | 305 | 305 | 305 | 305 | 305 |
| | spray tower (out) | 151 | 151 | 151 | 151 | 151 |
| | Filter (in) | 140 | 137 | 130 | 127 | 126 |
| | Scrubber (in) | 110 | 110 | 110 | 108 | 105 |
| | Scrubber (out) | 14 | 14 | 15 | 15 | 15 |
| Differential pressure/mbar | spray tower | 3.1 | 3 | 3 | 2.8 | 2.9 |
| | Filter | 1.7 | 1.7 | 1.8 | 1.8 | 2.1 |
| | Scrubber | 3.8 | 4.1 | 4.2 | 4.2 | 4.2 |
| Pressure/mbar | spray tower | −103 | −1.2 | −0.9 | −0.9 | −1.1 |
| Nozzle gas | Flow rate kg/h | 23 | 23 | 23 | 23 | 23 |
| | Temperature/° C. | r.t.*) | r.t.*) | r.t.*) | r.t.*) | r.t.*) |
| | Pressure/bar | 2.5 | 2.5 | 2.5 | 2.5 | 2.5 |

-continued

| Spray-dried product | Temperature/° C. | r.t.*) | r.t.*) | r.t.*) | r.t.*) | r.t.*) |
|---|---|---|---|---|---|---|

*)room temperature

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material thus obtained had a Zn content of 1.4 weight-%, a Ti content of 1.7 weight-%, a Si content of 41 weight-%, and a TOC content of <0.5 weight-%. The spray-dried product was then subjected to calcination for 2 h at 650° C. under air in a rotary furnace, yielding 43.8 kg of calcined spray-dried ZnTiMWW. The calcined spray-dried material thus obtained had a Zn content of 1.3 weight-%, a Ti content of 1.8 weight-%, a Si content of 42.5 weight-%, and a C content of <0.1 weight-%. The bulk density of the calcined spray-dried ZnTiMWW was 90 g/l (gram/liter). The mesopores of the micropowder had an average pore diameter (4V/A) of 20.2 nm as determined by Hg porosimetry according to DIN 66133. The macropores of the micropowder had an average pore diameter (4V/A) of 67.6 nm as determined by Hg porosimetry according to DIN 66133. The micropores of the ZnTiMWW contained in the micropowder had an average pore diameter of 1.06 nm as determined by nitrogen adsorption according to DIN 66134 (Horward-Kawazoe method). The Dv10 value of the particles of the micropowder was 4.10 micrometers. The Dv50 value of the particles of the micropowder was 8.19 micrometers. The Dv90 value of the particles of the micropowder was 14.05 micrometers. The degree of crystallization determined via XRD was (77+/−10) %, the average crystallite size 35.0 nm+/−10%. It was found that the crystalline phase exhibits a pure MWW structure. No other crystalline titania phases such as anatase, rutile or brookite, or crystalline zinc silicate ($Zn_2SiO_4$) such as willemite could be detected.

2.5 Preparation of Moldings Containing ZnTiMWW and Silica Binder

Starting from the calcined spray-dried ZnTiMWW material obtained according to 1.4 above, a molding was prepared, dried, and calcined. Therefor, 12 batches were prepared, each starting from 3.5 kg of the calcined spray-dried ZnTiMWW material obtained above, 0.226 kg Walocel™ (Walocel MW 15000 GB, Wolff Cellulosics GmbH & Co. KG, Germany), 2.188 kg Ludox® AS-40 and 6.6 l deionized water, as follows:

3.5 kg ZnTiMWW and 0.226 kg Walocel were subjected to kneading in an edge mill for 5 min. Then, during further kneading, 2.188 kg Ludox were added continuously. After another 10 min, addition of 6 l of deionized water was started. After another 30 min, further 0.6 l of deionized water were added. After a total time of 50 min, the kneaded mass had become extrudable. Thereafter, the kneaded mass was subjected to extrusion under 65-80 bar wherein the extruder was cooled with water during the extrusion process. Per batch, the extrusion time was in the range of from 15 to 20 min. The power consumption per batch during extrusion was 2.4 A. A die head was employed allowing for producing cylindrical strands having a diameter of 1.7 mm. At the die head out outlet, the strands were not subjected to a cutting to length. The strands thus obtained were dried for 16 h at 120° C. in a drying chamber under air. In total (sum of the 12 batches), 56 kg white strands with a diameter of 1.7 mm were obtained. 56 kg of the dried strands were subjected to calcination in a rotary furnace at 550° C. for 1 h under air, yielding 52 kg calcined strands. Thereafter, the strands were sieved (mesh size 1.5 mm), and the yield, after sieving, was 50.0 kg. The thus obtained moldings exhibited a bulk density of 322 g/l (gram per liter) and had a Zn content of 1.1 weight-%, a Ti content of 1.4 weight-%, a Si content of 43 weight-%, and a C content of <0.1 weight-%. The mesopores of the micropowder had an average pore diameter (4V/A) of 20.9 nm as determined by Hg porosimetry according to DIN 66133. The macropores of the micropowder had an average pore diameter (4V/A) of 50.0 nm as determined by Hg porosimetry according to DIN 66133. The degree of crystallization determined via XRD was (70+/−10) %, the average crystallite size 32.5 nm+/−10%. The crush strength of the moldings as determined according to the method using a crush strength test machine Z2.5/TS01S was 4.4 N (standard deviation: 0.5 N). The minimum value found when testing the 10 samples was 3.5 N, the maximum value 5.1 N. In the $^{29}Si$ MAS NMR, after the curve had been deconvolved by the proper Gaussian-Lorentzian line shapes, six peaks were clearly observed. The $Q^3/Q^4$ ratio was found to be 2.2. The total amount of adsorbed water as determined according to Reference Example 6 of the molding was 6.9 weight-%. The Langmuir surface are determined via nitrogen adsorption at 77 K according to DIN 66133 was 518 $m^2/g$, the mulitpoint BET specific surface area determined via nitrogen adsorption at 77 K according to DIN 66133 was 373 $m^2/g$. The total intrusion volume determined according to Hg porosimetry according to DIN 66133 was 1.3 ml/g (milliliter/gram), the respective total pore area 100.2 $m^2/g$. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Starting from the calcined strands, a post-treatment stage was performed as follows: 1,000 kg deionized water were filled in a vessel. Then, 50 kg of the calcined moldings were added. The vessel was closed (pressure-tight), and the obtained mixture was heated to a temperature of 145° C. within 1.5 h and kept at this temperature under autogenous pressure (about 3 bar) for 8 h. Then, the mixture was cooled for 2 h. The water-treated strands were subjected to filtration and washed with deionized water. The obtained strands were heated in a drying chamber under air within 1 h to a temperature of 120° C. and kept at this temperature for 16 h. Subsequently, the dried material was heated under air to a temperature of 450° C. within 5.5 h and kept at this temperature for 2 h. Thereafter, the strands were sieved (mesh size 1.5 mm), and the yield, after sieving, was 49.1 kg. The thus obtained water-treated moldings exhibited a bulk density of 332 g/l (gram per liter) and had a Zn content of 1.1 weight-%, a Ti content of 1.4 weight-%, a Si content of 42 weight-%, and a C content of <0.10 weight-%. The mesopores of the micropowder had an average pore diameter (4V/A) of 22.1 nm as determined by Hg porosimetry according to DIN 66133. The macropores of the micropowder had an average pore diameter (4V/A) of 52.0 nm as determined by Hg porosimetry according to DIN 66133. The degree of crystallization determined via XRD was (69+/−10) %, the average crystallite size 30.5 nm+/−10%. The crush strength of the moldings as determined according to the method using a crush strength test machine Z2.5/TS01S was 13.7 N (standard deviation: 2.5 N). The minimum value found when testing the 10 samples was 10.2 N, the maximum value 17.6 N. In the $^{29}$Si MAS NMR, after the curve had been deconvolved by the proper Gaussian-Lorentzian line shapes, six peaks were clearly observed. The $Q^3/Q^4$ ratio was found to be 1.39. The total amount of adsorbed water of the molding was 6.9 weight-%. The intensity ratio of the infrared band in the region of (3746+/−20) cm$^{-1}$ attributed to the free silanol groups, relative to the infrared band in the region of 3688+/−20 cm$^{-1}$ attributed to vicinal silanol groups was smaller than 1.4. The Langmuir surface are determined via nitrogen adsorption at 77 K according to DIN 66133 was 421 m$^2$/g, the multi-point BET specific surface area determined via nitrogen adsorption at 77 K according t DIN 66133 was 303 m$^2$/g. The total intrusion volume determined according to Hg porosimetry according to DIN 66133 was 1.3 ml/g (milliliter/gram), the respective total pore area 98.7 m$^2$/g. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Reference Example 3: Characterization of the Catalyst

Reference Example 3.1: Determination of Dv10, Dv50, and Dv90 Values 1.0 g of the micropowder is suspended in 100 g deionized water and stirred for 1 min. The sample was subjected to the measurement in an apparatus using the following parameters: Mastersizer S long bed version 2.15, ser. No. 33544-325; supplier: Malvern Instruments GmbH, Herrenberg, Germany: focal width 300 RF mm; beam length 10.00 mm; module MS017; shadowing 16.9%; dispersion model 3 $$D; analysis model polydisperse correction none.

Reference Example 3.2: Determination of the Silanol Concentration of the Moldings For the determination of the silanol concentration, the $^{29}$Si MAS NMR experiments were carried out at room temperature on a VARIAN Infinityplus-400 spectrometer using 5.0 mm ZrO$_2$ rotors. The $^{29}$Si MAS NMR spectra were collected at 79.5 MHz using a 1.9 μs π/4 (microsecond pi/4) pulse with 10 s recycle delay and 4000 scans. All $^{29}$Si spectra were recorded on samples spun at 6 kHz, and chemical shifts were referenced to 4,4-dimethyl-4-silapentane sulfonate sodium (DSS). For the determination of the silanol group concentration, a given $^{29}$Si MAS NMR spectrum is deconvolved by the proper Gaussian-Lorentzian line shapes. The concentration of the silanol groups with respect to the total number of Si atoms is obtained by integrating the deconvolved $^{29}$Si MAS NMR spectra.

Reference Example 3.3: Determination of the Crush Strength of the Moldings

The crush strength as referred to in the context of the present invention is to be understood as determined via a crush strength test machine Z2.5/TS01S, supplier Zwick GmbH & Co., D-89079 Ulm, Germany. As to fundamentals of this machine and its operation, reference is made to the respective instructions handbook "Register 1: Betriebsan- leitung/Sicherheitshandbuch für die Material-Prüfmaschine Z2.5/TS01S", version 1.5, December 2001 by Zwick GmbH & Co. Technische Dokumentation, August-Nagel-Strasse 11, D-89079 Ulm, Germany. With said machine, a given strand is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 3.4: $^{29}$Si Solid-State NMR Spectra Regarding $Q^3$ and $Q^4$ Structures The effect of the inventive water treatment on the molding related to $Q^3$ and $Q^4$ structures in the material was characterized by comparing the changes in $^{29}$Si solid-state NMR spectra under comparable conditions. All $^{29}$Si solid-state NMR experiments were performed using a Bruker Advance spectrometer with 300 MHz $^1$H Larmor frequency (Bruker Biospin, Germany). Samples were packed in 7 mm ZrO$_2$ rotors, and measured under 5 kHz Magic Angle Spinning at room temperature. $^{29}$Si direct polarization spectra were obtained using (pi/2)-pulse excitation with 5 microsecond pulse width, a $^{29}$Si carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethylsilyl M group to 12.5 ppm. The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus the clearly visible shoulder at −98 ppm. Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit. After the water treatment of the invention, a decrease of signal intensity at the left hand side of the spectrum was observed, a region that includes $Q^3$ silanol structures (here especially: around and above −104 ppm, i.e. "left" of −104 ppm). Further, an increase of signal at the right hand side of the spectrum (here: below −110 ppm, i.e. "right" of −110 ppm) was observed, which region comprises $Q^4$ structures exclusively. For the quantification of spectrum changes, a ratio was calculated that reflects changes in the peak areas "left hand" and "right hand", as follows. The six peaks were labeled with 1, 2, 3, 4, 5, and 6, and the ratio Q was calculated with the formula $100*\{[a_1+a_2]/[a_4+a_5+a_6]\}/a_3$. In this formula, $a_{i,\ i=1\ \ldots\ 6}$ represents the area of the fitted peak to which this number was attributed.

Reference Example 3.5: Water Adsorption/Desorption—Water Uptake

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 weight-%). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 weight-% from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 weight-% to 5 weight-% with a step of 10% and the change in the weight of the sample (water uptake) was monitored and recorded.

Reference Example 3.6: FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 $cm^{-1}$ region were analyzed and for comparing multiple samples, as reference the band at 1880±5 $cm^{-1}$ was taken.

Reference Example 3.7: Determination of Crystallinity via XRD

The crystallinity of the zeolitic materials according to the present invention were determined by XRD analysis. The data were collected using a standard Bragg-Brentano diffractometer with a Cu-X-ray source and an energy dispersive point detector. The angular range of 2° to 70° (2 theta) was scanned with a step size of 0.02°, while the variable divergence slit was set to a constant illuminated sample length of 20 mm. The data were then analyzed using TOPAS V4 software, wherein the sharp diffraction peaks were modeled using a Pawley fit containing a unit cell with the following starting parameters: a=14.4 Angstrom (1 Angstrom=$10^{-10}$ m) and c=25.2 Angstrom in the space group P6/mmm. These were refined to fit the data. Independent peaks were inserted at the following positions. 8.4°, 22.4°, 28.2° and 43°. These were used to describe the amorphous content. The crystalline content describes the intensity of the crystalline signal to the total scattered intensity. Included in the model were also a linear background, Lorentz and polarization corrections, lattice parameters, space group and crystallite size.

Reference Example 4: Epoxidation Process with ZnTiMWW Catalyst in Acetonitrile, Water A main reactor A was a vertically mounted tube-bundle reactor with 5 tubes (length of the tubes: 12 m, internal tube diameter: 38 mm), each tube being equipped with an axially placed multi-point thermocouple with 10 equally spaced measuring points encased in a suitable thermowell with a diameter of 18 mm. Each tube was charged with 3 kg of the ZnTiMWW catalyst moldings as prepared according to Reference Example 2. Free space eventually remaining was filled with steatite spheres (diameter of 3 mm). The heat of reaction was removed by circulating a thermostatized heat transfer medium (water/glycol mixture) on the shell side in co-current direction to the feed. The flow rate of the heat transfer medium was adjusted so that the temperature difference between entrance and exit did not exceed 1° C. The reaction temperature referred to hereinbelow, also referred to as $T^R$, was defined as the temperature of the heat transfer medium entering the reactor shell. At the reactor exit, the pressure was controlled by a pressure regulator and kept constant at 20 bar(abs). The output stream (5) leaving the epoxidation unit A was sampled every 20 minutes in order to determine the hydrogen peroxide concentration using the titanyl sulfate method and to calculate the hydrogen peroxide conversion. The hydrogen peroxide conversion was defined as $100\times(1-m_{out}/m_{in})$ wherein $m_{in}$ is the molar flow rate of $H_2O_2$ in the reactor feed and $m_{out}$ is the molar flow rate of $H_2O_2$ in the reactor outlet. Based on the respectively obtained hydrogen peroxide conversion values, the inlet temperature of the heat transfer medium was adjusted in order to keep the hydrogen peroxide conversion essentially constant in the range of from 90 to 92%. The inlet temperature of the heat transfer medium was set at 30° C. at the start of a given run with a fresh batch of the epoxidation catalyst and was increased, if necessary, to maintain the hydrogen peroxide conversion in the mentioned range. The required temperature increase was usually less than 1 K/d. The output stream (5) leaving the epoxidation unit A was passed through a heat exchanging unit. The stream leaving the heat exchanging unit was fed to Epoxidation Unit B.

Epoxidation in a Finishing Reactor (Epoxidation Unit B): The finishing reactor B was a fixed bed reactor operated adiabatically. In this context, the term "adiabatic" refers to an operation mode according to which no active cooling is carried out and according to which the finishing reactor is suitably insulated in order to minimize heat losses. The finishing reactor B had a length of 4 m and a diameter of 100 mm. The reactor was filled with 9 kg of the same epoxidation catalyst which was used in the main epoxidation reactor A. Spare space was filled with steatite spheres (diameter of 3 mm). The operating pressure of the finishing reactor B was 10 bar which was kept constant by a suitable pressure regulator at the reactor exit. The output of the finishing reactor B was sampled every 20 min in order to determine the hydrogen peroxide concentration using the titanyl sulfate method. The effluent of the finishing reactor B, stream (6), was preferably depressurized into a flash drum, and both the liquid and the gas from this drum were fed to a light boiler separation column (distillation unit C).

The main reactor A was fed from below with a liquid monophasic stream (1). Stream (1) was prepared by mixing five streams (2), (2a), (3), (4) and (4a). The temperature of stream (1) was in the range from 20 to 40° C. The streams were premixed at an absolute pressure of 23 bar. The liquid feed stream (1) consisted of one single liquid phase:

Stream (2) was an acetonitrile stream and had a flow rate of 69 kg/h.

Stream (2a) was a water stream and had a flow rate of 3 kg/h.

Stream (3) having a flow rate of 12.9 kg/h was a propylene stream (containing 0.35 kg/h propene) and was supplied from a storage tank, allowing for a continuous feeding, and fed using a suitable metering pump.

Stream (4) having a flow rate of 15 kg/h was an aqueous hydrogen peroxide solution having a hydrogen peroxide concentration of 40 weight-% ("crude/washed" grade from Solvay with a TOC in the range of 100 to 400 mg/kg). The aqueous hydrogen peroxide solution was supplied from a storage tank, allowing for a continuous feeding, and fed using a suitable metering pump.

Stream (4a) was an aqueous stream comprising dissolved potassium formate. The further stream was supplied from a storage tank, allowing for a continuous feeding, and was fed using a suitable metering pump. The concentration of the potassium formate was 2.5 weight-%, the feed rate of the stream was 500 g/h (1000 μmol potassium/mol hydrogen peroxide). Stream (4a) was thoroughly mixed with stream (4) before the combined stream was mixed with the stream resulting from mixing streams (2), 2a) and (3).

The epoxidation was performed in a continuous manner.

The reactor effluent stream downstream the pressure control valve was collected, weighed and analyzed (effluent stream (6)). Organic components, with the exception of oxygen, were analyzed in two separate gas-chromatographs. The hydrogen peroxide content was determined colorimetrically using the titanyl sulfate method. Effluent stream (6) comprised 66.5 weight-% acetonitrile, 17.4 weight-% water, 11.6 weight-% propylene oxide, 3.8 weight-% propylene, 0.13 weight-% propylene glycol, 0.5 weight-% propane, 0.03 weight-% oxygen, 0.02 weight-% acetaldehyde, 0.01 weight-% propionaldehyde.

Reference Example 5: Separation of Propene from Stream (6) to Obtain Stream S1

Separation of Light Boilers from Stream (6) to Obtain a Stream (7) (Stream S1)

Stream (6) was sent to a light boiler separation column (distillation unit C) operated at 1.1 bar. The distillation column had a length of 8.5 m, a diameter of 170 mm, and was equipped with 40 bubble trays, an evaporator at the bottom and a condenser at the top. The column was operated as a mixed washing/distillation tower, wherein the washing agent was taken from a separate tank or from a later process stage and was at 10° C. introduced at the top of the column. Liquid and gaseous inlet streams were introduced to the column at different points. The feed point of the liquid portion of stream (6) was above bubble tray 37; the gaseous portion of stream (6) was introduced into the column above bubble tray 28 (counted from the top). Stream (S8), which represented stream S2, was taken off of the light boiler separation column as bottoms stream. The gaseous stream (7) leaving the cooling means at the top of the column contained mainly propene, propane (which was contained as impurity in the polymer-grade propene used), and small amounts of $CO_2$ and $N_2$, and was essentially free of propylene oxide (less than 300 volume-ppm) as shown in Table 1. This top stream (7) represented stream S1.

TABLE 1

| Composition of stream S1 | | | | |
|---|---|---|---|---|
| Propene | Water | $CO_2$ | Propane | $N_2$ |
| 91 weight-% | 0 weight-% | 0.65 weight-% | 5.5 weight-% | 2.85 weight-% |

Reference Example 6: Epoxidation Process with TS-1 Catalyst in Methanol, Water

A main reactor A was a vertically mounted tube-bundle reactor with 5 tubes (length of the tubes: 12 m, internal tube diameter: 38 mm), each tube being equipped with an axially placed multi-point thermocouple with 10 equally spaced measuring points encased in a suitable thermowell with a diameter of 18 mm. Each tube was charged with 3 kg of the TS-1 catalyst moldings as prepared according to Reference Example 1. Free space eventually remaining was filled with steatite spheres (diameter of 3 mm). The heat of reaction was removed by circulating a thermostatized heat transfer medium (water/glycol mixture) on the shell side in co-current direction to the feed. The flow rate of the heat transfer medium was adjusted so that the temperature difference between entrance and exit did not exceed 1° C. The reaction temperature referred to herein below, also referred to as $T^R$, was defined as the temperature of the heat transfer medium entering the reactor shell. At the reactor exit, the pressure was controlled by a pressure regulator and kept constant at 20 bar(abs). The output stream (5) leaving the epoxidation unit A was sampled every 20 minutes in order to determine the hydrogen peroxide concentration using the titanyl sulfate method and to calculate the hydrogen peroxide conversion. The hydrogen peroxide conversion was defined as $100 \times (1-m_{out}/m_{in})$ wherein $m_{in}$ is the molar flow rate of $H_2O_2$ in the reactor feed and $m_{out}$ is the molar flow rate of $H_2O_2$ in the reactor outlet. Based on the respectively obtained hydrogen peroxide conversion values, the inlet temperature of the heat transfer medium was adjusted in order to keep the hydrogen peroxide conversion essentially constant in the range of from 90 to 92%. The inlet temperature of the heat transfer medium was set at 30° C. at the start of a given run with a fresh batch of the epoxidation catalyst and was increased, if necessary, to maintain the hydrogen peroxide conversion in the mentioned range. The required temperature increase was usually less than 1 K/d. Epoxidation in a Finishing Reactor (Epoxidation Unit B): The finishing reactor B was a fixed bed reactor operated adiabatically. In this context, the term "adiabatic" refers to an operation mode according to which no active cooling is carried out and according to which the finishing reactor is suitably insulated in order to minimize heat losses. The finishing reactor B had a length of 4 m and a diameter of 100 mm.

The reactor was filled with 9 kg of the same epoxidation catalyst which was used in the main epoxidation reactor A. Spare space was filled with steatite spheres (diameter of 3 mm). The operating pressure of the finishing reactor B was 10 bar which was kept constant by a suitable pressure regulator at the reactor exit. The output of the finishing reactor B was sampled every 20 min in order to determine the hydrogen peroxide concentration using the titanyl sulfate method. The effluent of the finishing reactor B, stream (6), was preferably depressurized into a flash drum, and both the liquid and the gas from this drum were fed to a light boiler separation column (distillation unit C).

The main reactor A was fed from below with a liquid monophasic stream (1). Stream (1) was prepared by mixing five streams (2), (2a), (3), (4) and (4a). The temperature of stream (1) was in the range from 20 to 40° C. The streams were premixed at an absolute pressure of 23 bar. The liquid feed stream (1) consisted of one single liquid phase:

Stream (2) was an MeOH stream and had a flow rate of 50.3 kg/h.
Stream (2a) was a water stream and had a flow rate of 0.2 kg/h.
Stream (3) having a flow rate of 9.4 kg/h was a propylene stream (containing 0.25 kg/h propene) and was supplied from a storage tank, allowing for a continuous feeding, and fed using a suitable metering pump.
Stream (4) having a flow rate of 14 kg/h was an aqueous hydrogen peroxide solution having a hydrogen peroxide concentration of 40 weight-% ("crude/washed" grade from Solvay with a TOC in the range of 100 to 400 mg/kg). The aqueous hydrogen peroxide solution was supplied from a storage tank, allowing for a continuous feeding, and fed using a suitable metering pump.
Stream (4a) was an aqueous stream comprising dissolved dipotassium hydrogenphosphate. The further stream was supplied from a storage tank, allowing for a continuous feeding, and was fed using a suitable metering pump. The concentration of the dipotassium hydrogenphosphate was 2.5 weight-%, the feed rate of the stream was 100 g/h (200 μmol potassium/mol hydrogen peroxide). Stream (4a) was thoroughly mixed with stream (4) before the combined stream was mixed with the stream resulting from mixing streams (2), 2a) and (3).

The epoxidation was performed in a continuous manner. The reactor effluent stream downstream the pressure control valve was collected, weighed and analyzed (effluent stream (6)). Organic components, with the exception of oxygen, were analyzed in two separate gaschromatographs. The hydrogen peroxide content was determined colorimetrically using the titanyl sulfate method. Effluent stream (6) comprised 66.1 weight-% MeOH, 17.2 weight-% water, 10.6 weight-% propylene oxide, 4.2 weight-% propylene, 0.5 weight-% propylene glycol, 0.24 weight-% propane, 0.04 weight-% oxygen, 0.08 weight-% acetaldehyde, 0.01 weight-% propionaldehyde.

Distillation Column K1

The reactor effluent from reactor A, the liquid and also the gaseous portion thereof (stream (5)) were passed to a distillation column K1 and distilled at ambient pressure. The distillation column (DN25×2600 mm length, PN 10) was made of stainless steel and equipped with a Sulzer CY packing. The distillation unit K1 was operated under ambient pressure and other operating conditions (heating of the bottoms, reflux ratio) were adjusted so that essentially all of the propylene oxide was contained in the top stream (5a); stream (5a) was sent to a light boiler separation column (distillation unit C). The bottoms stream (5b) contained about 75 wt.-% of methanol and essentially all of the non-reacted hydrogen peroxide.

This bottoms stream (5b) was passed through a heat exchanger and brought to a temperature of 35° C. Before this stream was introduced into reactor B, it was admixed with a propylene stream (4a) (polymer grade propylene containing 99.9 wt.-% propene, the remainder essentially being propane; flow rate: of 22.5 g/h).

Reference Example 7: Separation of Propene from Stream (6) to Obtain Stream S1

Separation of Light Boilers from Stream (6) to Obtain a Stream (7) (Stream S1)

Stream (6) from Reference Example 6 was sent to a light boiler separation column (distillation unit C) operated at 1.1 bar. The distillation column had a length of 8.5 m, a diameter of 170 mm, and was equipped with 40 bubble trays, an evaporator at the bottom and a condenser at the top. The column was operated as a mixed washing/distillation tower, wherein the washing agent was taken from a separate tank or from a later process stage and was at 10° C. introduced at the top of the column. Liquid and gaseous inlet streams were introduced to the column at different points. The feed point of the liquid portion of stream (6) was above bubble tray 37; the gaseous portion of stream (6) was introduced into the column above bubble tray 28 (counted from the top). Stream (S8), which represented stream S2, was taken off of the light boiler separation column as bottoms stream. The gaseous stream leaving the cooling means at the top of the propene separation column contained mainly propene, propane (which was contained as impurity in the polymer-grade propene used), and small amounts of $CO_2$ and $N_2$, and was essentially free of propylene oxide (less than 300 volume-ppm) as shown in Table 2. This top stream represented stream S1.

TABLE 2

| Composition of stream S1 of Reference Example 7 | | | | |
|---|---|---|---|---|
| Propene | Water | $CO_2$ | Propane | $N_2$ |
| 91 weight-% | 0 weight-% | 0.65 weight-% | 5.5 weight-% | 2.85 weight-% |

COMPARATIVE AND INVENTIVE EXAMPLES 1.1 Calculations

Regarding the recycling of propene from the off-gas mainly composed of propene, propane and carbon dioxide the relative capacity for the propene absorption and the relative selectivity against propane and CO2 was elaborated on the basis of limiting activity coefficients at 298K, calculated by Cosmo-RS (COSMOthermX, Version C30_1601, developed and copyright by COSMOlogic GmbH&Co.KG, Imbacher Weg 46, 51379 Leverkusen, GERMANY). The parametrization BP_TZVPD_FINE_C30_1601 was applied. The Cosmo-RS calculation is based on an activity coefficient model with ideal gas phase. Therefore the fugacity and the pressure effect on the gas phase is not considered, the activity coefficient is not depending on the pressure. Parting from the limiting activity coefficients at infinite dilution ($g^\infty(CO_2)$, $g^\infty$(Propane) and $g^\infty$(Propene)) at 25° C. selectivity (S) and capacity (KAP, KAPm mass based, considering the molar weight MW (g/mol) of the solvent mixture) criteria were calculated taking into account different amounts of water in the solvents acetonitrile or methanol. The following criteria were calculated:

$$S_1 = g^\infty(\text{Propane})/g^\infty(\text{Propene})$$

$$S_2 = g^\infty(\text{CO2})/g^\infty(\text{Propene})$$

$$KAP = 1/g^\infty(\text{Propene})$$

$$KAPm = 1/g^\infty(\text{Propene})/MW(\text{solvent mixture}) \cdot 1000$$

In Table 3 and Table 4 the limiting activity coefficients and the selectivity and capacity criteria (mass related capacity multiplied by 1000 for readability) are compiled with increasing water concentration (w(g/g) H₂O weight fraction of water) parting from the pure solvents acetonitrile or methanol. With increasing water concentration in acetonitrile and in methanol the capacity for the propene absorption is diminished and the selectivity against propane is enhanced.

TABLE 3

Parameters for acetonitrile - water solvent mixtures at 298 K

| w(g/g) H2O | KAPm | KAP | S1 | S2 | $g^\infty$ (Propene) | $g^\infty$ (Propane) | $g^\infty$ (CO2) |
|---|---|---|---|---|---|---|---|
| 0.00 | 4.7 | 0.19 | 2.7 | 0.16 | 5.2 | 13.9 | 0.8 |
| 0.10 | 3.6 | 0.13 | 2.8 | 0.16 | 7.7 | 21.3 | 1.2 |
| 0.20 | 2.6 | 0.09 | 2.9 | 0.15 | 11.7 | 33.9 | 1.8 |
| 0.30 | 1.8 | 0.05 | 3.0 | 0.15 | 18.3 | 55.0 | 2.7 |
| 0.40 | 1.3 | 0.03 | 3.1 | 0.14 | 29.1 | 90.9 | 4.2 |
| 0.50 | 0.9 | 0.02 | 3.3 | 0.14 | 46.8 | 152.5 | 6.5 |

TABLE 4

Parameters for methanol - water solvent mixtures at 298 K

| w(g/g) H2O | KAPm | KAP | S1 | S2 | $g^\infty$ (Propene) | $g^\infty$ (Propane) | $g^\infty$ (CO2) |
|---|---|---|---|---|---|---|---|
| 0.00 | 6.0 | 0.19 | 1.7 | 0.43 | 5.2 | 9.0 | 2.3 |
| 0.10 | 4.3 | 0.13 | 1.9 | 0.39 | 7.7 | 14.4 | 3.0 |
| 0.20 | 3.1 | 0.09 | 2.0 | 0.35 | 11.5 | 23.1 | 4.0 |
| 0.30 | 2.2 | 0.06 | 2.2 | 0.31 | 17.4 | 37.8 | 5.4 |
| 0.40 | 1.5 | 0.04 | 2.3 | 0.27 | 26.9 | 63.1 | 7.3 |
| 0.50 | 1.0 | 0.02 | 2.6 | 0.24 | 42.2 | 107.7 | 10.1 |

For the components propene and propane a well as for carbon dioxide and nitrogen a cubic equation od state model (NRTL mixing rule version of the PSRK equation of state, T. Holderbaum and J. Gmehling, PSRK: A Group Contribution Equation of State Based on UNIFAC, Fluid Phase Equilib. 70 (1991) pages 251-265) was created in order to account for the higher pressure range and the near- or supercritical conditions by applying experimental pure component data and experimental mixture data for the binary systems with acetonitrile or methanol. The addition of water to the respective solvent acetonitrile or methanol was considered by scaling the partial pressure of the solutes on a molar basis in a pure solvent by the limiting activity coefficient ratio calculated by Cosmo-RS for the water containing solvent in comparison to the pure solvent.

1.2 Simulations

The data of the comparative Example and the inventive Examples were obtained from simulations with program package AspenONE V8.6 (company Aspentech).

1.3 Scrubber Set-Up

The scrubber was a distillation tower, operated at a top pressure in the range of 6 to 30 bar, a sump pressure of 18 bar and was calculated with 20 theoretical trays (no reboiler, exclusive condenser). The feed point of stream S1 was at stage 6 counted from the top. Stream S1 from the light boiler separation (distillation unit C) or stream S1a from distillation unit D1 represented the feed stream S1 for all the examples as outlined in detail for each Example below and was feed with a temperature of 15° C. (temperature adjusted by heat exchanger) and a mass stream of 3710 kg/h and had the following composition: 91 weight-% propene (3458 kg/h), 0 weight-% water (0 kg/h), 0.65 weight-% carbon dioxide (24.7 kg/h), 5.5 weight-% propane (209 kg/h), 2.85 weight-% nitrogen (108.3 kg/h) in accordance with Tables 1, 2. Entraining agent (EA) was introduced at the top. The temperatures at the top and in the sump of the distillation tower are indicated in Tables 5-9. Stream S4 was taken off as top stream and introduced into a condenser. The concentration of propene in the stream S4 after passing the condenser was set to a loss 1 weight-% with respect to the amount of propene comprised in S1. Stream EA, used as entraining agent, contained acetonitrile and water as indicated in Tables 5 to 6 or methanol and water as indicated in Tables 7 to 9. This stream was fed to the top of the tower as a liquid with a temperature of 25° C. and a flow rate between 4-50 t/h (see examples).

1.4 Example 1: Acetonitrile—Water as Entraining Agent with Water Content in the Range of 0 to 20 Weight-%

Figure 4:
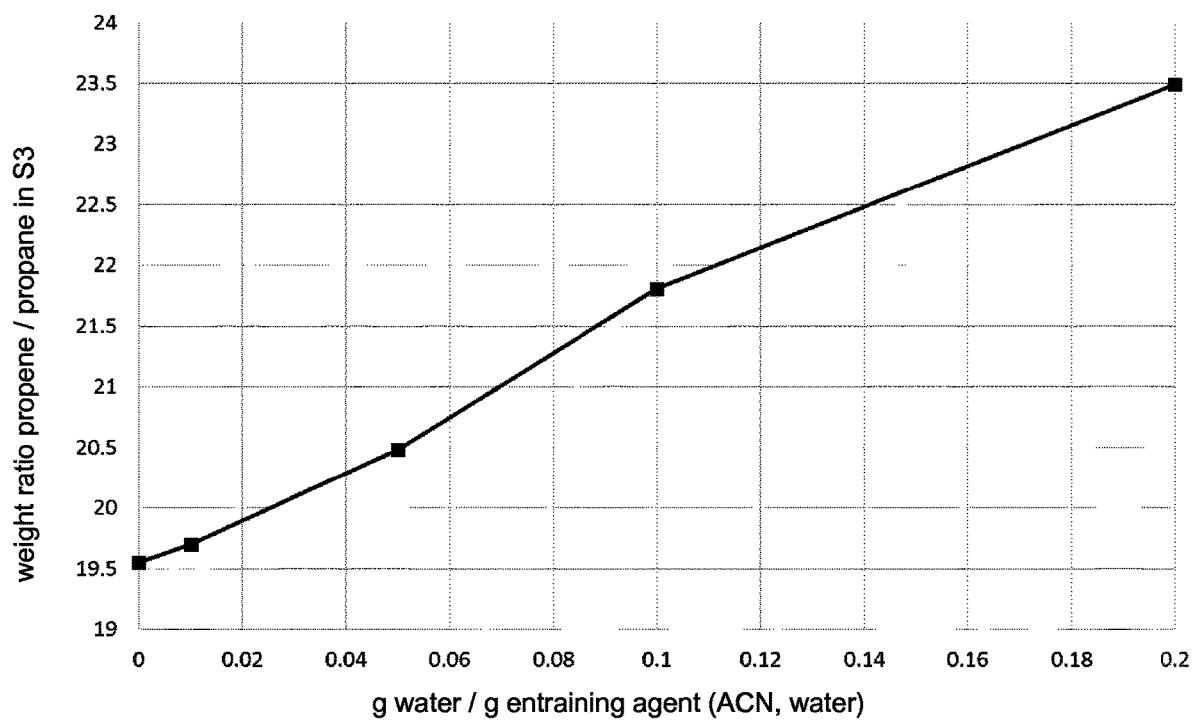

Stream S1 from the light boiler separation (distillation unit C) according to Reference Example 5 represented the feed stream S1. Pure acetonitrile (ACN) and mixtures of acetonitrile with water were used as entraining agent (stream EA) in a scrubber as described in 1.3. The concentrations of the solvent mixtures and the compositions of the condensed stream S4 and the bottoms stream S3 are indicated in Table 5. FIG. 4 shows the propene purity expressed as weight ratio propene/propane in stream S3 in relation to the water content of the entraining agent (weight fraction water [g/g]).

TABLE 5

Compositions of the bottoms stream S3 and the condensed stream S4 after condenser, entraining agent ACN with 0 to 20 weight-% water

| Entraining agent | | Sump | | | Stream S4 after condenser | | |
|---|---|---|---|---|---|---|---|
| ACN g/g | water g/g | Mass stream (kg/h) | Temperature in ° C. | pressure in bar | Mass stream (kg/h) | Mass stream (kg/h) | propene concentration (g/g) | propane concentration (g/g) |
| 1.00 | 0 | 11156.81 | 60.92 | 18.00 | 14779.85 | 176.96 | 0.20 | 0.19 |
| 0.99 | 0.01 | 11262.16 | 60.13 | 18.00 | 14883.83 | 178.34 | 0.19 | 0.20 |

TABLE 5-continued

Compositions of the bottoms stream S3 and the condensed stream S4
after condenser, entraining agent ACN with 0 to 20 weight-% water

| 0.95 | 0.05 | 11815.82 | 56.97 | 18.00 | 15430.87 | 184.95 | 0.19 | 0.23 |
| 0.90 | 0.10 | 12868.84 | 52.99 | 18.00 | 16473.86 | 194.99 | 0.18 | 0.27 |
| 0.80 | 0.20 | 14621.45 | 47.16 | 18.00 | 18206.87 | 206.21 | 0.17 | 0.29 |

| Entraining agent | | | Sump (stream S3) | |
| --- | --- | --- | --- | --- |
| ACN g/g | water g/g | Mass stream (kg/h) | Propene loss Propene top/ Propene feed | Propene/ Propane (=purity) |
| 1.00 | 0 | 11156.81 | 0.01 | 19.55 |
| 0.99 | 0.01 | 11262.16 | 0.01 | 19.70 |
| 0.95 | 0.05 | 11815.82 | 0.01 | 20.48 |
| 0.90 | 0.10 | 12868.84 | 0.01 | 21.81 |
| 0.80 | 0.20 | 14621.45 | 0.01 | 23.49 |

Surprisingly, it was found that increased water content in the entraining agent enables an improved separation of propene and propane. Thus, the use of a scrubber with entraining agent acetonitrile/water allows a recovery of propene in the sump, which can then be recycled to the process.

1.5 Example 2: Acetonitrile—Water as Entraining Agent, Water Content 10 Weight-%

Stream S1 from the light boiler separation (distillation unit C) according to Reference Example 5 represented the feed stream S1. A mixture of acetonitrile with water was used as entraining agent (stream EA) as in Example 1, with a weight ratio ACN:water=9:1.

The concentrations of the solvent mixture and the compositions of the condensed stream S4 and the bottoms stream S3 are indicated in Table 6.

TABLE 6

Compositions of the bottoms stream S3 and the condensed stream
S4 after condenser, entraining agent ACN with 10 weight-% water

| Entraining agent | | | Sump | | | Stream S4 after condenser | | |
| --- | --- | --- | --- | --- | --- | --- | --- | --- |
| ACN in g/g | Water in g/g | Mass stream in kg/h | Temperature in °C. | Pressure in bar | Mass stream in kg/h | Mass stream in kg/h | Propene in g/g | Propane in g/g |
| 0.90 | 0.10 | 48890.14 | 35.81 | 6.00 | 52462.45 | 227.68 | 0.15 | 0.45 |
| 0.90 | 0.10 | 41872.21 | 37.32 | 7.00 | 45448.90 | 223.30 | 0.15 | 0.44 |
| 0.90 | 0.10 | 36586.86 | 38.75 | 8.00 | 40167.88 | 218.98 | 0.16 | 0.43 |
| 0.90 | 0.10 | 32449.18 | 40.12 | 9.00 | 36034.47 | 214.72 | 0.16 | 0.43 |
| 0.90 | 0.10 | 29110.69 | 41.42 | 10.00 | 32700.19 | 210.50 | 0.16 | 0.42 |
| 0.90 | 0.10 | 26350.54 | 42.66 | 11.00 | 29944.24 | 206.30 | 0.17 | 0.41 |
| 0.90 | 0.10 | 24021.77 | 43.84 | 12.00 | 27619.64 | 202.12 | 0.17 | 0.40 |
| 0.90 | 0.10 | 22022.39 | 44.97 | 13.00 | 25624.44 | 197.95 | 0.17 | 0.40 |
| 0.90 | 0.10 | 20279.04 | 46.04 | 14.00 | 23885.27 | 193.77 | 0.18 | 0.39 |
| 0.90 | 0.10 | 18736.99 | 47.06 | 15.00 | 22347.42 | 189.57 | 0.18 | 0.38 |
| 0.90 | 0.10 | 17353.68 | 48.03 | 16.00 | 20968.35 | 185.32 | 0.19 | 0.37 |
| 0.90 | 0.10 | 16093.88 | 48.92 | 17.00 | 19712.88 | 181.01 | 0.19 | 0.37 |
| 0.90 | 0.10 | 14924.91 | 49.74 | 18.00 | 18548.34 | 176.57 | 0.20 | 0.36 |
| 0.90 | 0.10 | 13696.05 | 50.59 | 19.00 | 17324.52 | 171.53 | 0.20 | 0.35 |
| 0.90 | 0.10 | 12137.37 | 51.62 | 20.00 | 15772.52 | 164.85 | 0.21 | 0.33 |
| 0.90 | 0.10 | 10716.24 | 52.69 | 21.00 | 14358.12 | 158.12 | 0.22 | 0.31 |
| 0.90 | 0.10 | 9660.72 | 54.01 | 22.00 | 13308.25 | 152.47 | 0.23 | 0.29 |
| 0.90 | 0.10 | 8760.36 | 55.41 | 23.00 | 12413.18 | 147.18 | 0.23 | 0.28 |
| 0.90 | 0.10 | 7965.86 | 56.86 | 24.00 | 11623.74 | 142.12 | 0.24 | 0.27 |
| 0.90 | 0.10 | 7252.28 | 58.36 | 25.00 | 10915.08 | 137.20 | 0.25 | 0.25 |
| 0.90 | 0.10 | 6603.53 | 59.90 | 26.00 | 10271.15 | 132.38 | 0.26 | 0.24 |
| 0.90 | 0.10 | 5992.21 | 61.53 | 27.00 | 9664.74 | 127.47 | 0.27 | 0.22 |
| 0.90 | 0.10 | 5412.57 | 63.25 | 28.00 | 9089.95 | 122.62 | 0.28 | 0.20 |
| 0.90 | 0.10 | 4873.45 | 65.01 | 29.00 | 8555.47 | 117.98 | 0.29 | 0.18 |
| 0.90 | 0.10 | 4369.19 | 66.82 | 30.00 | 8055.73 | 113.46 | 0.30 | 0.16 |

TABLE 6-continued

Compositions of the bottoms stream S3 and the condensed stream
S4 after condenser, entraining agent ACN with 10 weight-% water

| Entraining agent | | | | | Sump (stream S3) |
| --- | --- | --- | --- | --- | --- |
| ACN in g/g | Water in g/g | Mass stream in kg/h | Sump Pressure in bar | Propene loss Propene top/ Propene feed | Propene/ Propane (=purity) |
| 0.90 | 0.10 | 48890.14 | 6.00 | 0.01 | 31.94 |
| 0.90 | 0.10 | 41872.21 | 7.00 | 0.01 | 30.92 |
| 0.90 | 0.10 | 36586.86 | 8.00 | 0.01 | 29.99 |
| 0.90 | 0.10 | 32449.18 | 9.00 | 0.01 | 29.13 |
| 0.90 | 0.10 | 29110.69 | 10.00 | 0.01 | 28.34 |
| 0.90 | 0.10 | 26350.54 | 11.00 | 0.01 | 27.60 |
| 0.90 | 0.10 | 24021.77 | 12.00 | 0.01 | 26.91 |
| 0.90 | 0.10 | 22022.39 | 13.00 | 0.01 | 26.26 |
| 0.90 | 0.10 | 20279.04 | 14.00 | 0.01 | 25.65 |
| 0.90 | 0.10 | 18736.99 | 15.00 | 0.01 | 25.08 |
| 0.90 | 0.10 | 17353.68 | 16.00 | 0.01 | 24.53 |
| 0.90 | 0.10 | 16093.88 | 17.00 | 0.01 | 24.00 |
| 0.90 | 0.10 | 14924.91 | 18.00 | 0.01 | 23.49 |
| 0.90 | 0.10 | 13696.05 | 19.00 | 0.01 | 22.91 |
| 0.90 | 0.10 | 12137.37 | 20.00 | 0.01 | 22.11 |
| 0.90 | 0.10 | 10716.24 | 21.00 | 0.01 | 21.39 |
| 0.90 | 0.10 | 9660.72 | 22.00 | 0.01 | 20.85 |
| 0.90 | 0.10 | 8760.36 | 23.00 | 0.01 | 20.39 |
| 0.90 | 0.10 | 7965.86 | 24.00 | 0.01 | 19.99 |
| 0.90 | 0.10 | 7252.28 | 25.00 | 0.01 | 19.63 |
| 0.90 | 0.10 | 6603.53 | 26.00 | 0.01 | 19.31 |
| 0.90 | 0.10 | 5992.21 | 27.00 | 0.01 | 18.94 |
| 0.90 | 0.10 | 5412.57 | 28.00 | 0.01 | 18.56 |
| 0.90 | 0.10 | 4873.45 | 29.00 | 0.01 | 18.24 |
| 0.90 | 0.10 | 4369.19 | 30.00 | 0.01 | 17.97 |

It was surprisingly found that a pressure increase from 5 up to 30 bar results in an increase of the uptake capacity of the ACN/water mixture for C3 compounds, i.e. propene and propane, in that the amount of entraining agent needed could be lowered to less than 10% of the initial amount at 5 bar.

1.6 Example 3: Methanol—Water as Entraining Agent, Water Content 10 Weight-%

Stream S1 from the light boiler separation (distillation unit C) according to Reference Example 6 represented the feed stream S1. A mixture of methanol with water was used as entraining agent (stream EA) as in Example 1, with a weight ratio MeOH:water=9:1. Contrary to Example 1, the sump pressure was set at 15 bar, the propene loss was set at 5% by weight and the scrubber had 40 theoretical trays (no reboiler and exclusive condenser).

Figure 5:
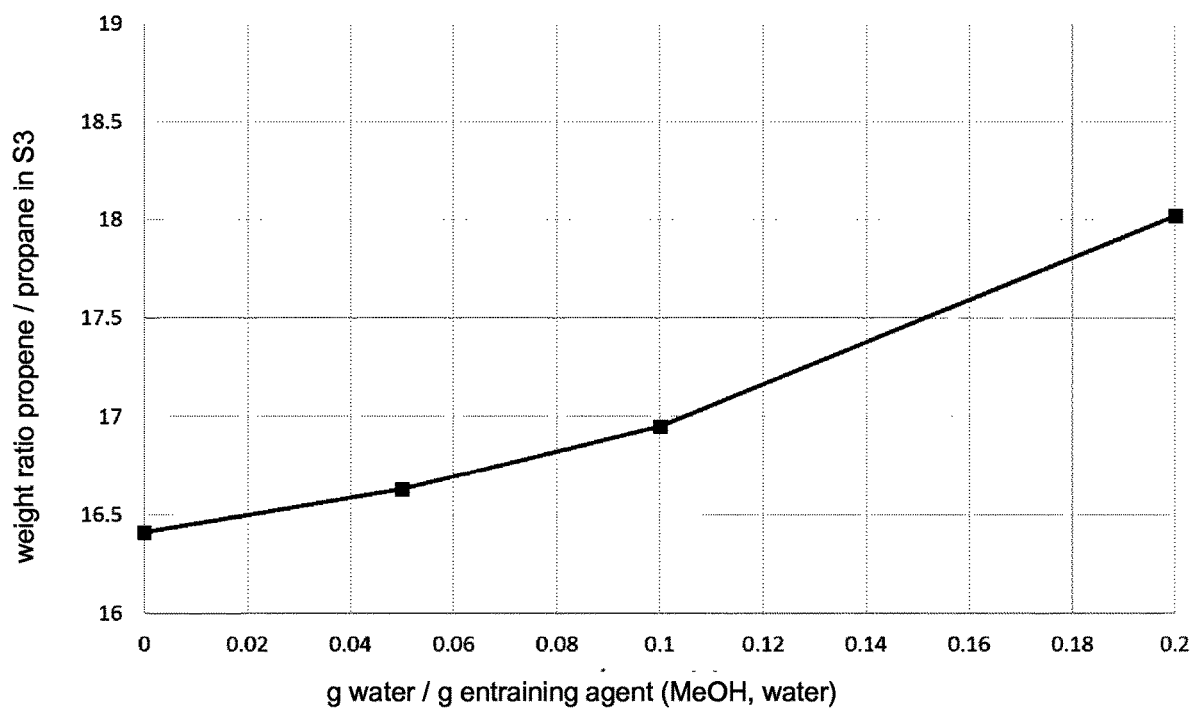

The concentrations of the solvent mixture and the compositions of the bottoms stream S3 and the condensed stream S4 are indicated in Table 7. FIG. 5 shows the propene purity expressed as weight ratio propene/propane in stream S3 in relation to the water content of the entraining agent (weight fraction water [g/g]).

TABLE 7

Compositions of the bottoms stream S3 and the condensed stream S4
after condenser, entraining agent MeOH with 0 to 20 weight-% water

| Entraining agent | | | Sump | | | Stream S4 after condenser | | |
| --- | --- | --- | --- | --- | --- | --- | --- | --- |
| MeOH g/g | water g/g | Mass stream (kg/h) | Temperature in ° C. | pressure in bar | Mass stream (kg/h) | Mass stream (kg/h) | propene concentration (g/g) | propane concentration (g/g) |
| 1.00 | 0.00 | 9709.07 | 51.47 | 16.00 | 13220.25 | 288.82 | 0.60 | 0.03 |
| 0.95 | 0.05 | 11665.55 | 46.93 | 16.00 | 15177.35 | 288.20 | 0.60 | 0.04 |
| 0.90 | 0.10 | 18234.62 | 42.72 | 16.00 | 17794.27 | 288.00 | 0.60 | 0.05 |
| 0.80 | 0.20 | 23696.33 | 35.55 | 16.00 | 27206.43 | 289.91 | 0.60 | 0.09 |

| Entraining agent | | | | Sump (stream S3) |
| --- | --- | --- | --- | --- |
| MeOH g/g | water g/g | Mass stream (kg/h) | Propene loss Propene top/ Propene feed | Propene/ Propane (=purity) |
| 1.00 | 0.00 | 9709.07 | 0.05 | 16.41 |
| 0.95 | 0.05 | 11665.55 | 0.05 | 16.63 |

TABLE 7-continued

Compositions of the bottoms stream S3 and the condensed stream S4 after condenser, entraining agent MeOH with 0 to 20 weight-% water

| 0.90 | 0.10 |          | 0.05 | 16.95 |
| 0.80 | 0.20 | 23696.33 | 0.05 | 18.02 |

Surprisingly, it was found that increased water content in the entraining agent enables a (improved) separation of propene and propane. Thus, the use of a scrubber with entraining agent acetonitrile/water allows a recovery of propene in the sump, which can then be recycled to the process.

1.7 Example 4: Methanol—Water as Entraining Agent, Water Content 10 Weight-%

Stream S1 from the light boiler separation (distillation unit C) according to Reference Example 6 represented the feed stream S1. A mixture of MeOH with water was used as entraining agent (stream EA) as in Example 3, with a weight ratio MeOH:water=9:1. The propene loss was set at 1 weight-%. The concentrations of the solvent mixture and the compositions of the bottoms stream S3 and the condensed stream S4 are indicated in Table 8.

Also here, it was found that a pressure increase from 5 to 30 bar resulted in a decrease of the amount of entraining agent need. However, when using methanol/water, the purity of propene slightly decreases with increasing pressure.

1.8 Example 5: Methanol—Water as Entraining Agent

Stream S1 from the light boiler separation (distillation unit C) according to Reference Example 6 represented the feed stream S1. A mixture of MeOH with water was used as entraining agent (stream EA) as in Example 4 with a weight ratio MeOH:water=8:2. The propene loss was set at 3 weight-%.

The concentrations of the solvent mixture and the compositions of the bottoms stream S3 and the condensed stream S4 are indicated in Table 9.

TABLE 8

Compositions of the bottoms stream S3 and the condensed stream S4 after condenser, entraining agent MeOH with 10 weight-% water

| Entraining agent | | | sump | | | Stream S4 after condenser | | |
| --- | --- | --- | --- | --- | --- | --- | --- | --- |
| MeOH in g/g | Water in g/g | Mass stream in kg/h | Temperature in ° C. | pressure in bar | Mass stream in kg/h | Mass stream in kg/h | Propene in g/g | Propane n in g/g |
| 0.8 | 0.2 | 52124.24 | 27.23 | 5.00 | 56324.23 | 142.36 | 0.24 | 0.11 |
| 0.8 | 0.2 | 41171.53 | 32.12 | 10.00 | 44829.75 | 141.78 | 0.24 | 0.11 |
| 0.8 | 0.2 | 36710.51 | 32.83 | 11.00 | 40369.18 | 141.33 | 0.24 | 0.11 |
| 0.8 | 0.2 | 32993.74 | 33.55 | 12.00 | 36652.91 | 140.83 | 0.25 | 0.11 |
| 0.8 | 0.2 | 29845.70 | 34.25 | 13.00 | 33505.43 | 140.27 | 0.25 | 0.12 |
| 0.8 | 0.2 | 27140.85 | 34.95 | 14.00 | 30801.22 | 139.62 | 0.25 | 0.12 |
| 0.8 | 0.2 | 24786.47 | 35.63 | 15.00 | 28447.57 | 138.90 | 0.25 | 0.12 |
| 0.8 | 0.2 | 21324.63 | 36.96 | 16.00 | 24987.95 | 136.69 | 0.25 | 0.12 |
| 0.8 | 0.2 | 17169.20 | 39.21 | 17.00 | 20836.81 | 132.40 | 0.26 | 0.10 |
| 0.8 | 0.2 | 13944.83 | 41.59 | 18.00 | 17614.73 | 130.10 | 0.27 | 0.07 |
| 0.8 | 0.2 | 11524.88 | 43.83 | 19.00 | 15196.64 | 128.25 | 0.27 | 0.05 |
| 0.8 | 0.2 | 9498.05 | 45.88 | 20.00 | 13171.86 | 126.19 | 0.27 | 0.04 |
| 0.8 | 0.2 | 4359.15 | 54.12 | 25.00 | 6045.25 | 122.32 | 0.28 | 0.04 |
| 0.8 | 0.2 | 2975.09 | 61.53 | 30.00 | 4125.84 | 118.31 | 0.30 | 0.03 |

| Entraining agent | | | | | Sump (stream S3) |
| --- | --- | --- | --- | --- | --- |
| MeOH in g/g | Water in g/g | Mass stream in kg/h | sump pressure in bar | Propene loss Propene top/ Propene feed | Propene/ Propane (=purity) |
| 0.80.8 | 0.2 | 52124.24 | 5.00 | 0.01 | 18.34 |
| 0.80.8 | 0.2 | 41171.53 | 10.00 | 0.01 | 17.68 |
| 0.80.8 | 0.2 | 36710.51 | 11.00 | 0.01 | 17.70 |
| 0.80.8 | 0.2 | 32993.74 | 12.00 | 0.01 | 17.73 |
| 0.80.8 | 0.2 | 29845.70 | 13.00 | 0.01 | 17.75 |
| 0.80.8 | 0.2 | 27140.85 | 14.00 | 0.01 | 17.78 |
| 0.80.8 | 0.2 | 24786.47 | 15.00 | 0.01 | 17.79 |
| 0.80.8 | 0.2 | 21324.63 | 16.00 | 0.01 | 17.72 |
| 0.80.8 | 0.2 | 17169.20 | 17.00 | 0.01 | 17.43 |
| 0.80.8 | 0.2 | 13944.83 | 18.00 | 0.01 | 17.08 |
| 0.80.8 | 0.2 | 11524.88 | 19.00 | 0.01 | 16.87 |
| 0.80.8 | 0.2 | 9498.05 | 20.00 | 0.01 | 16.75 |
| 0.80.8 | 0.2 | 4359.15 | 25.00 | 0.01 | 16.11 |
| 0.80.8 | 0.2 | 2975.09 | 30.00 | 0.01 | 15.25 |

TABLE 9

Compositions of the bottoms stream S3 and the condensed stream
S4 after condenser, entraining agent MeOH with 20 weight-%
water; propene loss 1 and 3 weight-% respectively

| Entraining agent | | Mass stream in kg/h | sump | | Stream S4 after condenser | | | |
|---|---|---|---|---|---|---|---|---|
| MeOH in g/g | Water in g/g | | Temperature in ° C. | pressure in bar | Mass stream in kg/h | Mass stream in kg/h | Propene in g/g | Propane n in g/g |
| 0.8 | 0.2 | 9205.07 | 45.88 | 20.00 | 12803.58 | 201.49 | 0.51 | 0.05 |
| 0.8 | 0.2 | 9498.05 | 45.88 | 20.00 | 13171.86 | 126.19 | 0.27 | 0.04 |

| Entraining agent | | | | Sump (=purity) |
|---|---|---|---|---|
| MeOH in g/g | Water in g/g | Mass stream in kg/h | Propene loss Propene top/ Propene feed | (stream S3) Propene/ Propane |
| 0.8 | 0.2 | 9205.07 | 0.03 | 16.80 |
| 0.8 | 0.2 | 9498.05 | 0.01 | 16.75 |

Surprisingly, it was found that despite a higher loss of propene, i.e. 3 instead of 1%, the propene purity in the bottoms stream was increased.

1.9 Example 6: Acetonitrile—Water as Entraining Agent with Scrubber D2 and Downstream Distillation Unit D1

A gaseous stream (7) from the lights separation unit C having a composition as shown in Table 10 was used.

TABLE 10

| Composition of stream (7) | | | | |
|---|---|---|---|---|
| Propene | Water | $CO_2$ | Propane | $N_2$ |
| 85 weight-% | 0.3 weight-% | 0.6 weight-% | 10 weight-% | 4.1 weight-% |

Stream (7) as in Table 10 was sent to a distillation unit D1 operated at a sump pressure of 25 bar, a sump temperature of 68° C. and a top temperature of 55° C., which was calculated with 90 theoretical trays (including one reboiler). Stream (7) was introduced above theoretical tray 28, counted from top at a temperature of 69° C. Stream (9) was taken off via a side take off above theoretical tray 8, counted from top and contained mainly propene, propane and was enriched in propene compared to the stream (7) (mass stream ratio propene:propane in (9)=16). The liquid bottoms stream (11) taken off at the sump of D1 had a mass stream ratio propene:propane of 0.06, containing 0.4% of the propene introduced in S1.

Top stream S1a from the distillation unit D1, containing 6.2% of the propene introduced in S1 was sent to the scrubber D2. Contrary to the scrubber set-up outlined in 1.3 above, the scrubber D2 had 5 theoretical trays and the entraining agent was added at tray one, counted from top, with a temperature of 17.5° C. The scrubber was operated with a temperature a the top of 18.1° C., a sump temperature of 41.3° C., and a sump pressure of 24 bar. A mixture of acetonitrile with water was used as entraining agent (stream EA) with a weight ratio ACN:water=8:2. The ratios of the individual streams and the propene/propane ratios are indicated below:

Distillation Unit D1:
Stream (9) (S1b): ratio propene/propane=16
Ratio stream (7)/stream (10) (S1a)=10.2 (mass streams ratio)
Scrubber D2:
Stream S3: ratio propene/propane=23.43
Ratio stream S4/stream EA=0.26 (mass streams ratio)
Ratio stream (9) (S1b)/stream S3=28 (mass streams ratio)
Ratio stream/S1 (S1a)=0.26 (mass streams ratio)

1.10 Comparative Example 1: No Entraining Agent

Instead of a scrubber as described in "1.3 Reference Example" a simple distillation tower with internal reflux was used for Comparative Example 1 which was operated at a top pressure of 24.1 bar, a sump pressure of 25 bar and was calculated with 90 theoretical trays (inclusive 1 tray reboiler). The feed point of stream S1 was at stage 28 counted from the top. Stream S1 from the light boiler separation which represented the feed stream had a composition as indicated in Table 11 and was feed to the distillation tower with a temperature of 69° C. The temperatures at the top and in the sump of the distillation tower were 55 and 68° C. respectively. Stream S4 which consisted mainly of propene was taken off as side stream at stage 8 counted from top. The concentrations in the condensed stream S4 were measured and corresponded to a ratio propene/propane (mass stream) of 16 (=purity). No entraining agent was feed to the distillation tower.

TABLE 11

| Composition of stream S1 of Comparative Example 1 | | | | |
|---|---|---|---|---|
| Propene (weight-%) | Water (weight-%) | $CO_2$ (weight-%) | Propane (weight-%) | $N_2$ (weight-%) |
| 85 | 0.3 | 0.62 | 10 | 4.1 |

The ratios of the individual streams and the propene/propane ratios are indicated below:
ratio feed/top stream (Mass stream): 10.2
ratio feed/side take off S4 (Mass stream): 1.13
ratio feed/bottoms stream (Mass stream): 16.4
ratio Propene/Propane in top stream (Mass stream): 3.79
ratio Propene/Propane in bottoms stream (Mass stream): 0.09

Propene contained in top or bottoms stream was considered as lost. The relative propene loss was calculated to be 6.6%.

1.11 Comparative Example 2: No Entraining Agent

Instead of a scrubber as described in "1.3 Reference Example" a simple distillation tower with internal reflux was used for Comparative Example 2. which was operated at a top pressure of 42.1 bar. a sump pressure of 25 bar and was calculated with 90 theoretical trays (inclusive 1 tray reboiler). The temperatures at the top and in the sump of the distillation tower were 54 and 65° C. respectively.

The feed point of stream S1 was at stage 30 counted from the top. Stream S1 from the light boiler separation. which represented the feed stream. had a composition as indicated in Table 12 and was feed to the distillation tower with a temperature of 74° C. Stream S4. which consisted mainly of propene. was taken off as side stream at stage 5. counted from top. The concentrations in the condensed stream S4 were measured and corresponded to a ratio propene/propane (mass stream) of 14 (=purity). No entraining agent was feed to the distillation tower.

TABLE 12

Composition of stream S1 of Comparative Example 1

| Propene (weight-%) | Water (weight-%) | $CO_2$ (weight-%) | Propane (weight-%) | $N_2$ (weight-%) |
|---|---|---|---|---|
| 91.1 | 0.3 | 0.7 | 5.4 | 2.5 |

The ratios of the individual streams and the propene/propane ratios are indicated below:
 ratio feed/top stream (Mass stream): 10.5
 ratio feed/side take off S4 (Mass stream): 1.17
 ratio feed/bottoms stream (Mass stream): 18.3
 ratio Propene/Propane in top stream (Mass stream): 105.5
 ratio Propene/Propane in bottoms stream (Mass stream): 0.42

Propene contained in top or bottoms stream was considered as lost. The relative propene loss was calculated to be 8.1%.

SHORT DESCRIPTION OF THE FIGURES

Figure 2:
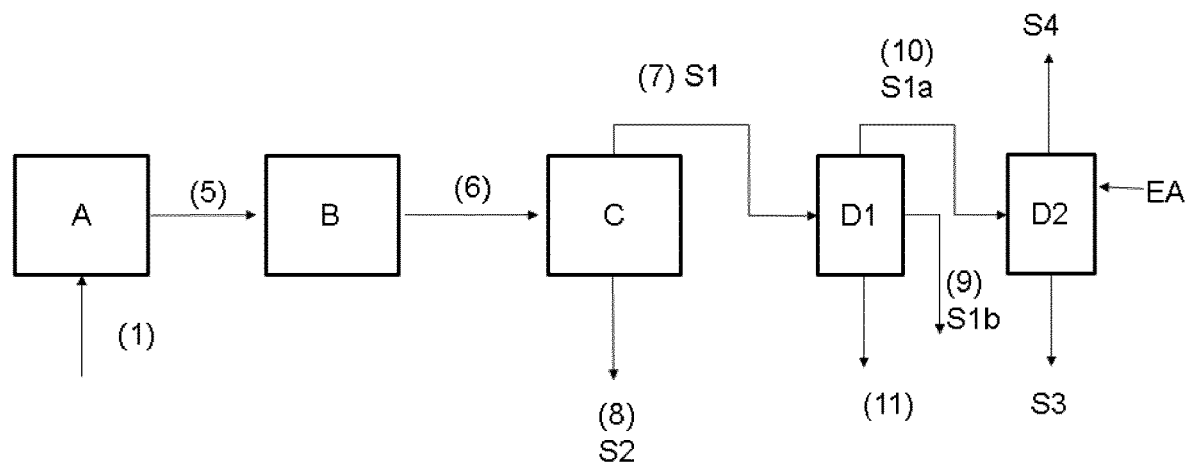
Figure 3:
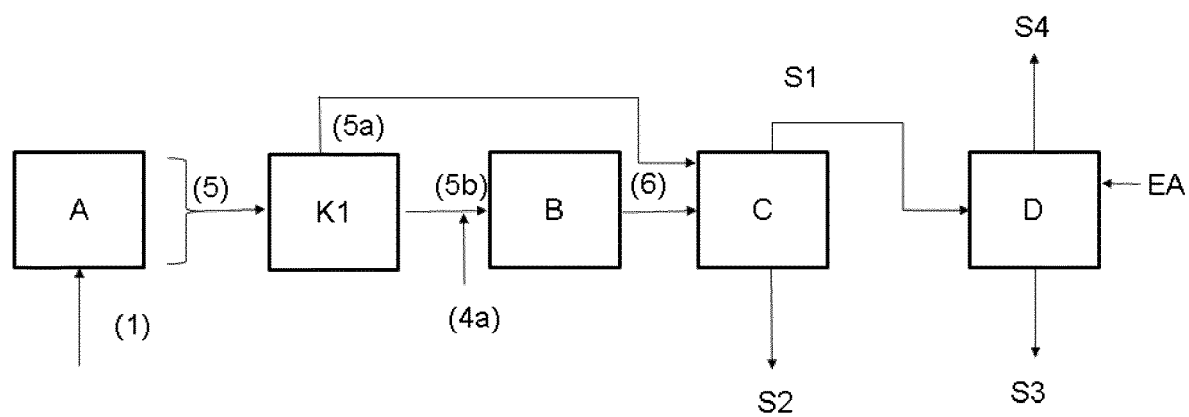

FIG. 1 shows a block diagram of the process according to the present invention with a distillation unit C for lights separation and a scrubber D. In FIG. 1, the letters and numbers have the following meanings:
 A epoxidation unit A
 B epoxidation unit B
 C distillation unit
 D scrubber
 EA entraining agent
 (1)-(8) streams according to a specifically preferred process as described in the examples
 S1, S3, S4 streams according to a preferred process as described in the general description and the examples
FIG. 2 shows a block diagram of the process according to the present invention with a two stage separation zone after the distillation unit C for lights separation comprising a distillation unit D1 and a scrubber D2. In FIG. 2, the letters and numbers have the following meanings:
 A epoxidation unit A
 B epoxidation unit B
 C distillation unit
 D1 distillation unit
 D2 scrubber
 EA entraining agent
 (1)-(11) streams according to a specifically preferred process as described in the examples
 S1, S1a, S1b,
 S3, S4 streams according to a preferred process as described in the general description and the examples
FIG. 3 shows a block diagram of the process according to the present invention with a distillation column K1 between first epoxidation zone A and second epoxidation zone B. In FIG. 3, the letters and numbers have the following meanings:
 A epoxidation unit A
 B epoxidation unit B
 C distillation unit
 D scrubber
 EA entraining agent
 K1 distillation unit
 (1)-(8) streams according to a specifically preferred process as described in the examples
 S1, S3, S4 streams according to a preferred process as described in the general description and the examples
FIG. 4 shows the propene purity expressed as weight ratio propene/propane in stream S3 (y-axis) in relation to the water content of the entraining agent (weight fraction water [g/g]; x-axis) of Example 1 (entraining agent: mixtures of water, acetonitrile (ACN))
FIG. 5 shows the propene purity expressed as weight ratio propene/propane in stream S3 (y-axis) in relation to the water content of the entraining agent (weight fraction water [g/g]; x-axis) of Example 3 (entraining agent: mixtures of water, methanol (MeOH))

CITED LITERATURE

WO 2004/037802 A1
WO 02/102496 A1
EP 1 122 246 A1
EP 1 485 366 B1
EP 1 122 249 A1
WO 2015/049327 A1
T. Holderbaum and J. Gmehling, PSRK: A Group Contribution Equation of State Based on UNIFAC, Fluid Phase Equilib. 70 (1991) pages 251-265

The invention claimed is:
1. A process for preparing propylene oxide, comprising
 (i) providing a stream comprising propene, propane, hydrogen peroxide or a source of hydrogen peroxide, water, and an organic solvent;
 (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and the organic solvent;
 (iii) removing an effluent stream from the epoxidation zone, the effluent stream comprising propene, propane, propylene oxide, water, and the organic solvent;
 (iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and organic solvent compared to the effluent stream subjected to distillation conditions;

(v) separating propane from the stream S1 in a separation zone, comprising subjecting the stream S1 to washing conditions in a scrubber, wherein a solvent mixture comprising organic solvent and water is added as entraining agent, obtaining a bottoms stream S3, which comprises organic solvent, water and at least 70 weight-% of the propene comprised in S1; and a gaseous top stream S4, which comprises at least 5 weight-% of the propane comprised in stream S1.

2. The process of claim 1, wherein the solvent mixture comprising organic solvent and water added as entraining agent in (v) has a capacity KAP with regard to propene at 25° C. in the range from 0.01 to 0.2.

3. The process of claim 1, wherein the solvent mixture comprising organic solvent and water added as entraining agent in (v) has a mass based capacity $KAP_m$ with regard to propene at 25° C. in the range from 4.4 to 10.

4. The process of claim 1, wherein the solvent mixture comprising organic solvent and water added as entraining agent in (v) has a selectivity S with regard to propene at 25° C. in the range from 1.3 to 3.5.

5. The process of claim 1, wherein the organic solvent comprised in the solvent mixture added as entraining agent in (v) is the same organic solvent as comprised in the stream provided in (i).

6. The process of claim 1, wherein the solvent mixture added as entraining agent in (v) comprises at least 0.1 weight-%, of water based on the total weight of the solvent mixture.

7. The process of claim 1, comprising
(i) providing a stream comprising propene, propane, hydrogen peroxide or a source of hydrogen peroxide, water, and acetonitrile;
(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and acetonitrile;
(iii) removing an effluent stream from the epoxidation zone, the effluent stream comprising propene, propane, propylene oxide, water, and acetonitrile;
(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;
(v) separating propane from the stream S1 in a separation zone, comprising subjecting the stream S1 to washing conditions in a scrubber, wherein a solvent mixture comprising acetonitrile and water is added as entraining agent, obtaining a bottoms stream S3, which comprises acetonitrile, water and at least 70 weight-% of the propene comprised in S1; and a gaseous top stream S4, which comprises at least 5 weight-% of the propane comprised in stream S1.

8. The process of claim 1, comprising
(i) providing a stream comprising propene, propane, hydrogen peroxide or a source of hydrogen peroxide, water, and methanol;
(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and methanol;
(iii) removing an effluent stream from the epoxidation zone, the effluent stream comprising propene, propane, propylene oxide, water, and methanol;
(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and methanol compared to the effluent stream subjected to distillation conditions;
(v) separating propane from the stream S1 in a separation zone, comprising subjecting the stream S1 to washing conditions in a scrubber, wherein a solvent mixture comprising methanol and water is added as entraining agent, obtaining a bottoms stream S3, which comprises methanol, water and at least 70 weight-% of the propene comprised in S1; and a gaseous top stream S4, which comprises at least 5 weight-% of the propane comprised in stream S1.

9. The process of claim 1, wherein the scrubber employed in (v) is a column, having from 2 to 20 theoretical trays.

10. The process of claim 1, wherein the solvent mixture comprising organic solvent and water added as entraining agent to the scrubber employed in (v) is added at a theoretical tray above the feed tray of the stream S1, counted from the top.

11. The process of claim 1, wherein the scrubber is operated at a top temperature in the range of 10 to 30° C.; and wherein the scrubber employed in (v) is operated at a sump pressure in the range of 1 to 35 bar.

12. The process of claim 1, wherein the separation zone in (v) comprises a distillation unit and the scrubber, wherein
(v.i) propane is separated from the gaseous stream S1 by distillation in the distillation unit comprised in the separation zone, obtaining a gaseous stream S1a, which is enriched in propene compared to the stream S1 subjected to distillation conditions, a gaseous stream S1b, which is enriched in propene compared to the stream S1 subjected to distillation conditions, and a bottoms stream S1c, which is depleted of propene compared to the stream S1 subjected to distillation conditions; and
(v.ii) subjecting the gaseous stream S1a obtained in (v.i) to washing conditions in the scrubber comprised in the separation zone, wherein a solvent mixture comprising organic solvent and water is added as entraining agent, obtaining the bottoms stream S3, which comprises organic solvent, water and at least 70 weight-% of the propene comprised in S1; and the gaseous top stream S4, which comprises at least 5 weight-% of the propane comprised in stream S1.

13. The process of claim 1, comprising
(i) providing a stream comprising propene, propane, hydrogen peroxide or a source of hydrogen peroxide, water, and acetonitrile;
(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and acetonitrile;

(iii) removing an effluent stream from the epoxidation zone, the effluent stream comprising propene, propane, propylene oxide, water, and acetonitrile;

(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and acetonitrile compared to the effluent stream subjected to distillation conditions;

(v) separating propane from the stream S1 in a separation zone, wherein the separation zone in (v) comprises a distillation unit and the scrubber, wherein (v.i) propane is separated from the gaseous stream S1 by distillation in the distillation unit comprised in the separation zone, obtaining a gaseous stream S1a, which is enriched in propene compared to the stream S1 subjected to distillation conditions, a gaseous stream S1b, which is enriched in propene compared to the stream S1 subjected to distillation conditions, and a bottoms stream S1c, which is depleted of propene compared to the stream S1 subjected to distillation conditions; and (v.ii) subjecting the gaseous stream Sla obtained in (v.i) to washing conditions in the scrubber comprised in the separation zone, wherein a solvent mixture comprising acetonitrile and water is added as entraining agent, obtaining the bottoms stream S3, which comprises acetonitrile, water and at least 70 weight-% of the propene comprised in S1; and the gaseous top stream S4, which comprises at least 5 weight-% of the propane comprised in stream S1.

14. The process of claim 1, comprising
(i) providing a stream comprising propene, propane, hydrogen peroxide or a source of hydrogen peroxide, water, and methanol;

(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and methanol;

(iii) removing an effluent stream from the epoxidation zone, the effluent stream comprising propene, propane, propylene oxide, water, and methanol;

(iv) separating propene and propane from the effluent stream by distillation, comprising subjecting the effluent stream to distillation conditions in a distillation unit, obtaining a gaseous stream S1 which is enriched in propene and propane compared to the effluent stream subjected to distillation conditions, and a liquid bottoms stream S2 which is enriched in propylene oxide, water and methanol compared to the effluent stream subjected to distillation conditions;

(v) separating propane from the stream S1 in a separation zone, wherein the separation zone in (v) comprises a distillation unit and the scrubber, wherein (v.i) propane is separated from the gaseous stream S1 by distillation in the distillation unit comprised in the separation zone, obtaining a gaseous stream S1a, which is enriched in propene compared to the stream S1 subjected to distillation conditions, a gaseous stream S1b, which is enriched in propene compared to the stream S1 subjected to distillation conditions, and a bottoms stream S1c, which is depleted of propene compared to the stream S1 subjected to distillation conditions; and (v.ii) subjecting the gaseous stream Sla obtained in (v.i) to washing conditions in the scrubber comprised in the separation zone, wherein a solvent mixture comprising methanol and water is added as entraining agent, obtaining the bottoms stream S3, which comprises methanol, water and at least 70 weight-% of the propene comprised in S1; and the gaseous top stream S4, which comprises at least 5 weight-% of the propane comprised in stream S1.

15. The process of claim 1, which is a continuous process.

* * * * *